United States Patent
Guggisberg et al.

(10) Patent No.: US 10,308,381 B2
(45) Date of Patent: Jun. 4, 2019

(54) CAP SUPPLY FOR VESSELS CONTAINING BIOLOGICAL SAMPLES

(71) Applicant: Roche Molecular Systems, Inc., Pleasanton, CA (US)

(72) Inventors: Thomas Guggisberg, Boswil (CH); Christian Kaelin, Brunn en (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 565 days.

(21) Appl. No.: 14/269,969

(22) Filed: May 5, 2014

(65) Prior Publication Data

US 2014/0331618 A1 Nov. 13, 2014

(30) Foreign Application Priority Data

May 8, 2013 (EP) ..................................... 13167057

(51) Int. Cl.
*B65B 7/28* (2006.01)
*B65D 85/62* (2006.01)
(Continued)

(52) U.S. Cl.
CPC .............. *B65B 7/2807* (2013.01); *B65B 7/28* (2013.01); *G01N 35/0099* (2013.01); *B65D 85/62* (2013.01); *G01N 2035/0405* (2013.01)

(58) Field of Classification Search
CPC .................... B65B 7/28; B65B 7/2807; G01N 2035/0405; A61M 5/008; B65D 85/62
(Continued)

(56) References Cited

U.S. PATENT DOCUMENTS 1,008,963 A * 11/1911 Ekermeyer .............. B65D 5/58
206/499
1,305,908 A * 6/1919 Lanier .................. B65D 85/321
206/499
(Continued)

FOREIGN PATENT DOCUMENTS

JP 2002518257 6/2002
JP 2003081441 A 3/2003
(Continued)

*Primary Examiner* — Thanh K Truong
*Assistant Examiner* — Patrick B Fry
(74) *Attorney, Agent, or Firm* — Pamela C. Ancona; M. Reza Savari

(57) ABSTRACT

A method for capping vessels containing biological samples is described providing a cap supply with a plurality of caps for the vessels within compartments in a predefined geometrical arrangement. The cap supply is introduced through an interface into a preanalytical system including a housing, and is reversibly docked to a feeder for inserting the cap supply into the preanalytical system and retrieving it therefrom. Subsequently, a cap is retrieved from the supply by a robotic manipulator, and transported to a workstation holding the vessels. A vessel is then capped using the manipulator. The steps from introducing the cap supply into the preanalytical system to capping a vessel are repeated a certain number of times or until all caps of the supply have been retrieved. Finally, the cap supply is retrieved from the preanalytical system. A preanalytical system and a cap supply for capping vessels containing biological samples is also provided.

4 Claims, 23 Drawing Sheets

(51) Int. Cl.
*G01N 35/04* (2006.01)
*G01N 35/00* (2006.01)

(58) Field of Classification Search
USPC .................................................. 53/287, 485
See application file for complete search history.

(56) References Cited

U.S. PATENT DOCUMENTS

| | | | | |
|---|---|---|---|---|
| 2,965,226 A * | 12/1960 | Ettlinger, Jr. | ........... | A47L 19/04 206/503 |
| 3,369,659 A * | 2/1968 | Ettlinger, Jr. | ........... | B65D 71/70 206/503 |
| 3,797,648 A * | 3/1974 | Shaw | ........... | B65D 71/00 206/277 |
| 3,937,322 A * | 2/1976 | Cohen | ........... | B01L 9/543 206/216 |
| 3,997,057 A * | 12/1976 | Craig | ........... | B65D 5/509 206/507 |
| 4,130,978 A * | 12/1978 | Cohen | ........... | B01L 9/543 206/499 |
| 4,722,440 A * | 2/1988 | Johnston | ........... | B65D 71/70 206/319 |
| 4,763,787 A * | 8/1988 | Koenig | ........... | B65D 19/20 206/418 |
| 5,036,001 A * | 7/1991 | Gork | ........... | G01N 33/02 435/286.2 |
| 5,479,969 A * | 1/1996 | Hardie | ........... | B65B 3/003 141/103 |
| 5,846,489 A | 12/1998 | Bienhaus et al. | | |
| 6,164,044 A * | 12/2000 | Porfano | ........... | B65B 55/10 422/28 |
| 6,164,449 A * | 12/2000 | Lahti | ........... | B01L 9/543 206/443 |
| 6,286,678 B1 * | 9/2001 | Petrek | ........... | B01L 9/543 206/443 |
| 6,673,316 B1 | 1/2004 | Okamoto et al. | | |
| 7,421,831 B2 | 9/2008 | Neeper et al. | | |
| 7,556,777 B2 * | 7/2009 | Victor | ........... | G01N 1/312 422/560 |
| 8,439,414 B2 * | 5/2013 | Neeper | ........... | B25J 9/102 294/119.1 |
| 8,453,838 B2 * | 6/2013 | Hill | ........... | A61M 5/008 206/438 |
| 8,703,492 B2 * | 4/2014 | Self | ........... | G01N 35/04 422/63 |
| 8,978,344 B2 * | 3/2015 | Krauss | ........... | B65B 3/003 53/281 |
| 9,156,598 B2 * | 10/2015 | Nicoletti | ........... | A61M 5/002 |
| 2005/0058574 A1 | 3/2005 | Bysouth et al. | | |
| 2005/0173295 A1 * | 8/2005 | Muraoka | ........... | B65D 57/00 206/593 |
| 2007/0007291 A1 * | 1/2007 | Gunn | ........... | B65D 1/36 220/23.86 |
| 2009/0298160 A1 | 12/2009 | Tajima et al. | | |
| 2010/0180551 A1 * | 7/2010 | Duethorn | ........... | B65B 7/2821 53/467 |
| 2011/0089709 A1 * | 4/2011 | Neeper | ........... | B25J 9/102 294/119.1 |
| 2011/0100268 A1 * | 5/2011 | Milkowski | ........ | B65D 19/0002 108/55.3 |
| 2011/0192756 A1 * | 8/2011 | Hill | ........... | A61M 5/008 206/515 |
| 2013/0048531 A1 * | 2/2013 | Nicoletti | ........... | A61M 5/002 206/557 |
| 2013/0174520 A1 * | 7/2013 | Tessier | ........... | B65B 3/003 53/452 |
| 2013/0255832 A1 | 10/2013 | Uchida | | |
| 2014/0331618 A1 | 11/2014 | Guggisberg et al. | | |
| 2017/0058321 A1 | 3/2017 | Tajima | | |

FOREIGN PATENT DOCUMENTS

| | | | | |
|---|---|---|---|---|
| JP | 2003098179 A | 4/2003 | | |
| JP | 2005003426 A | 1/2005 | | |
| WO | WO9965779 A1 | 12/1999 | | |
| WO | WO 2011092427 A1 * | 8/2011 | ........... | B65B 3/003 |
| WO | WO2012105712 A1 | 8/2012 | | |
| WO | 2012118141 A1 | 9/2012 | | |

* cited by examiner

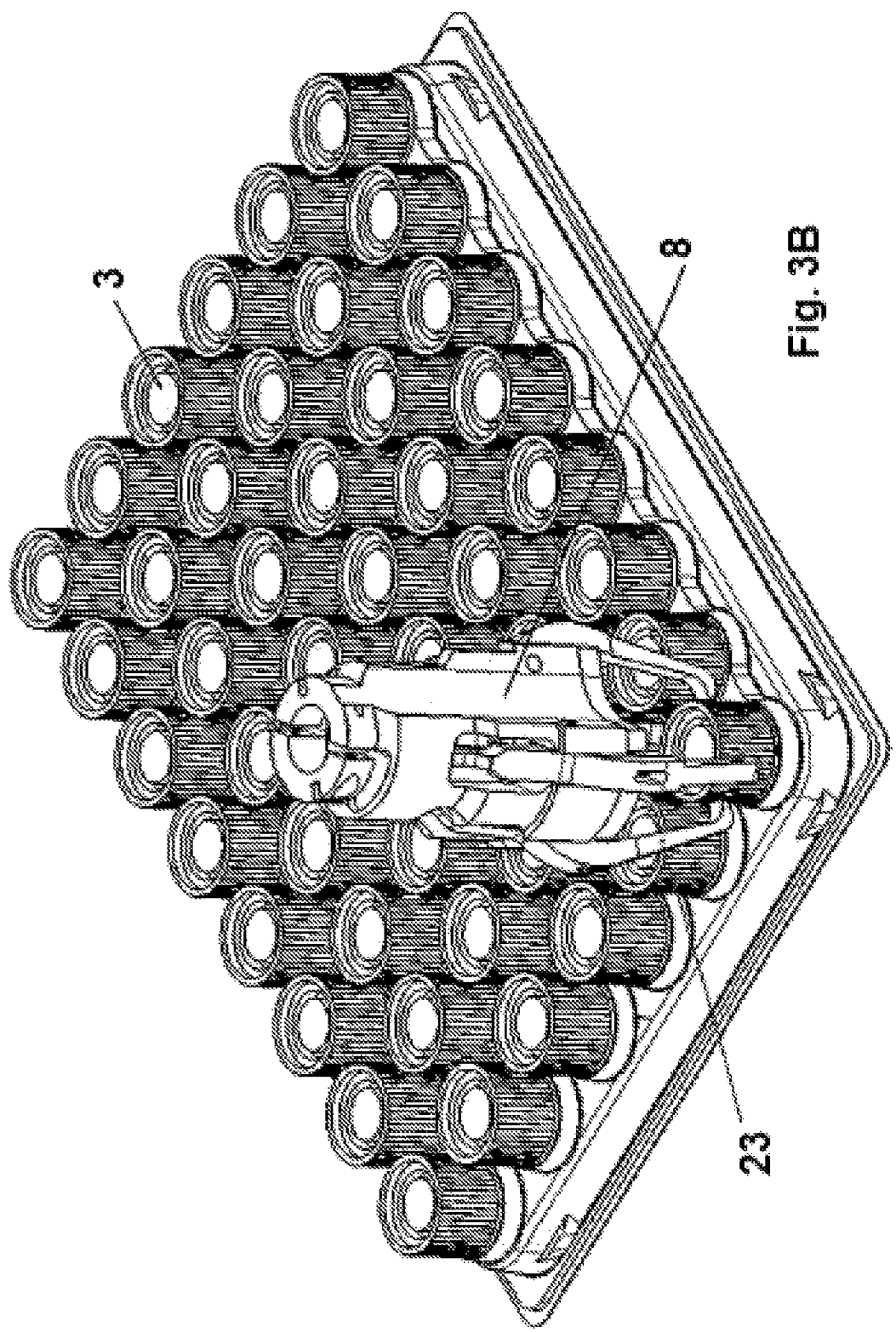

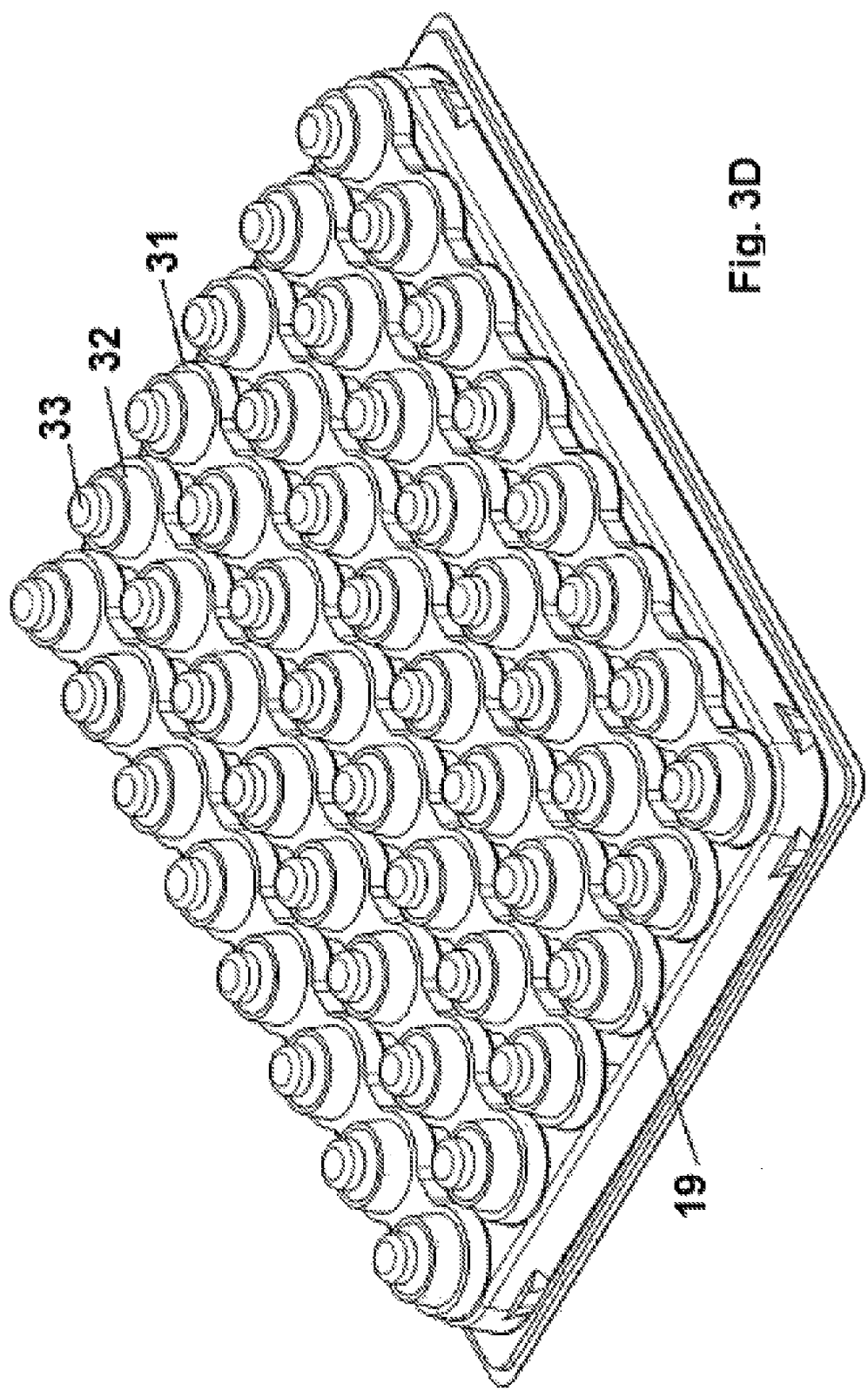

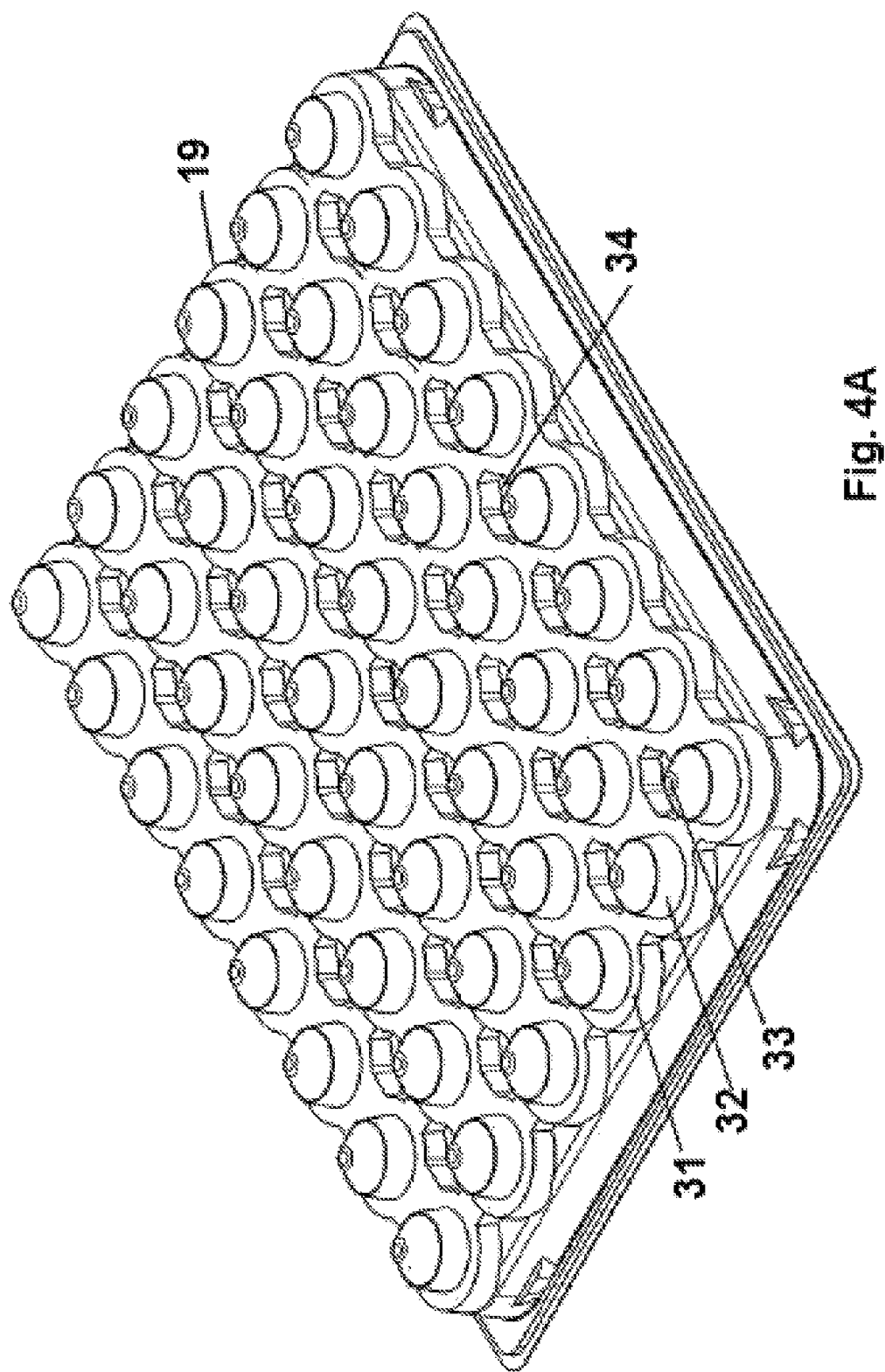

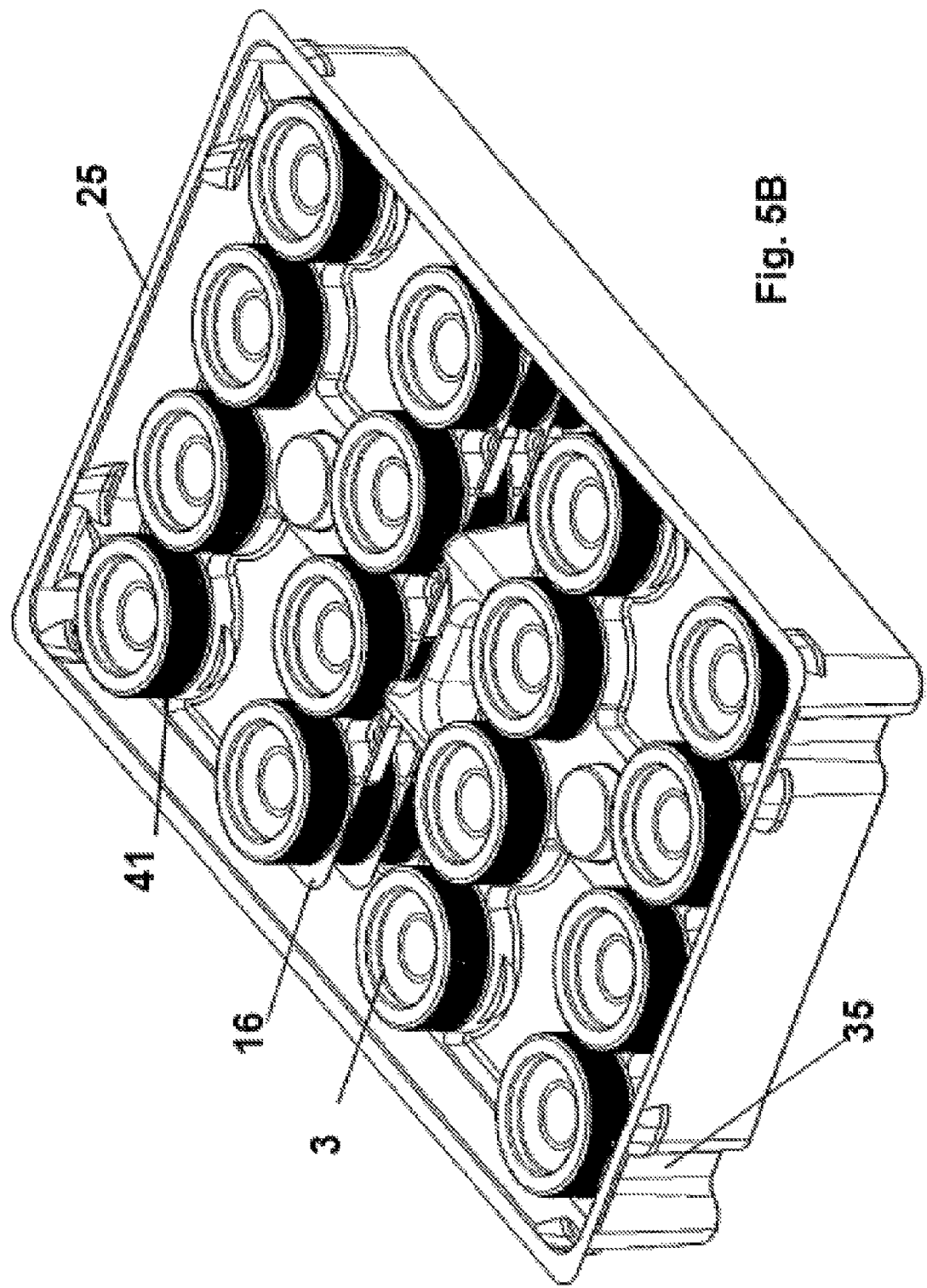

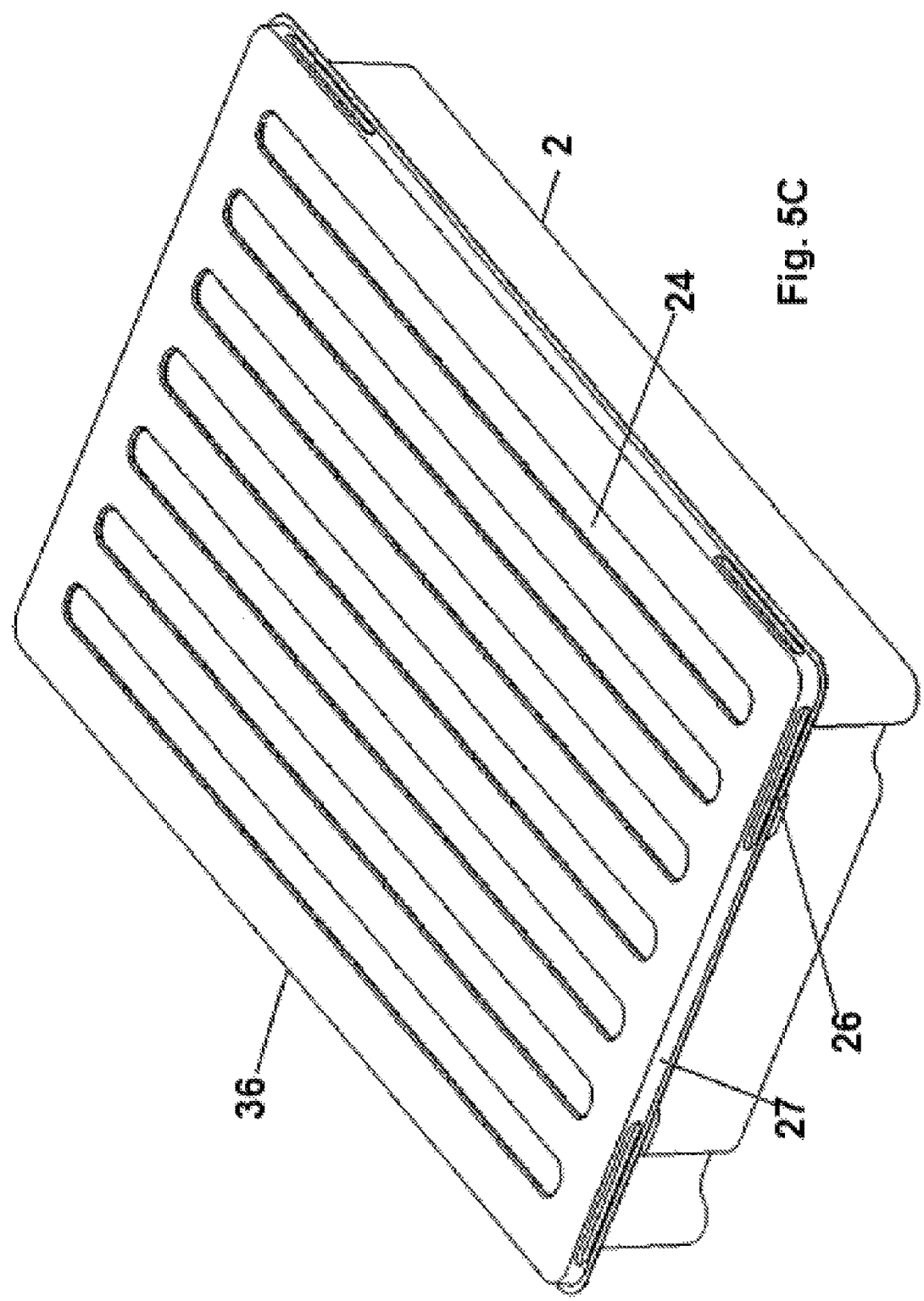

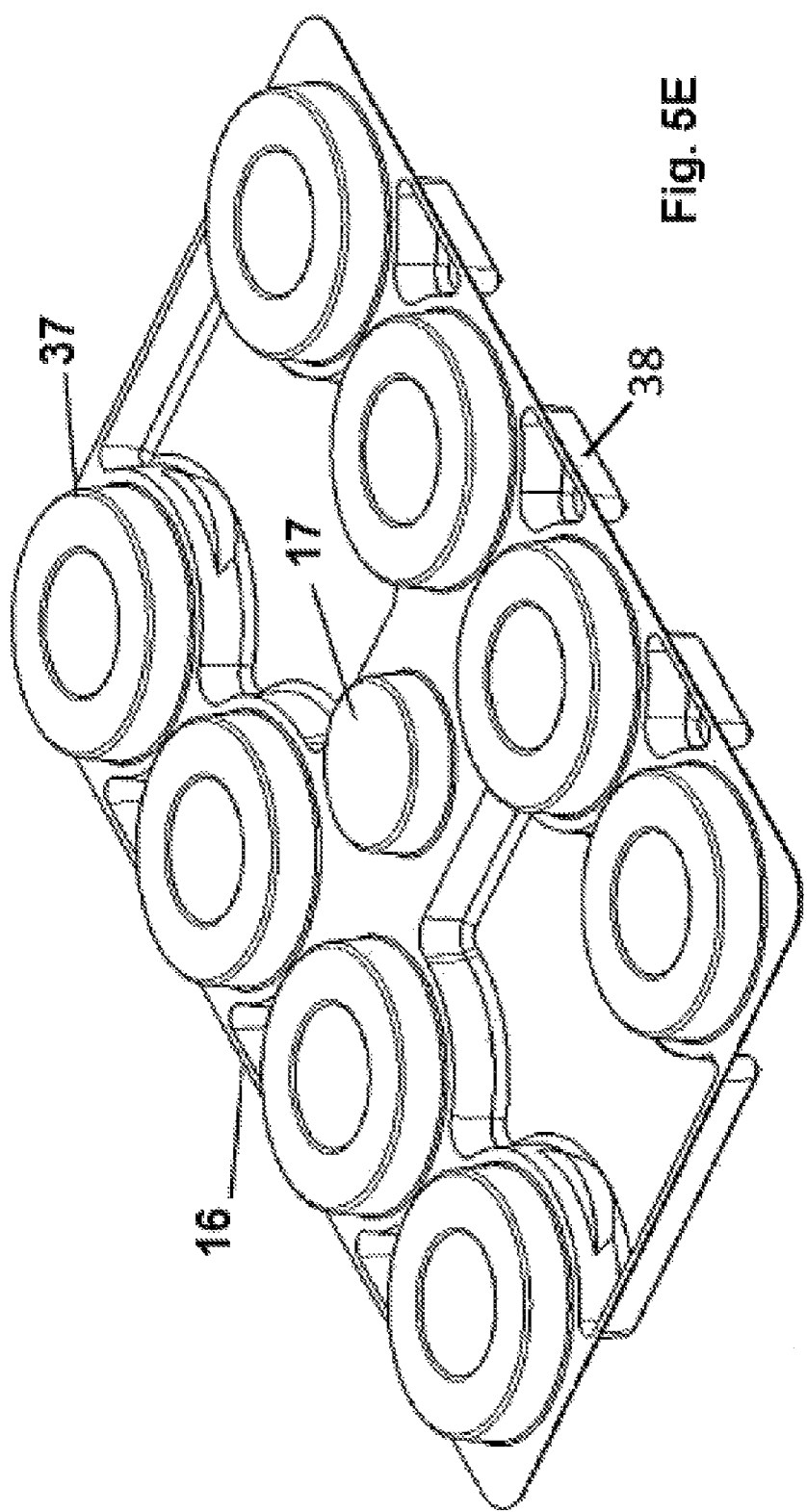

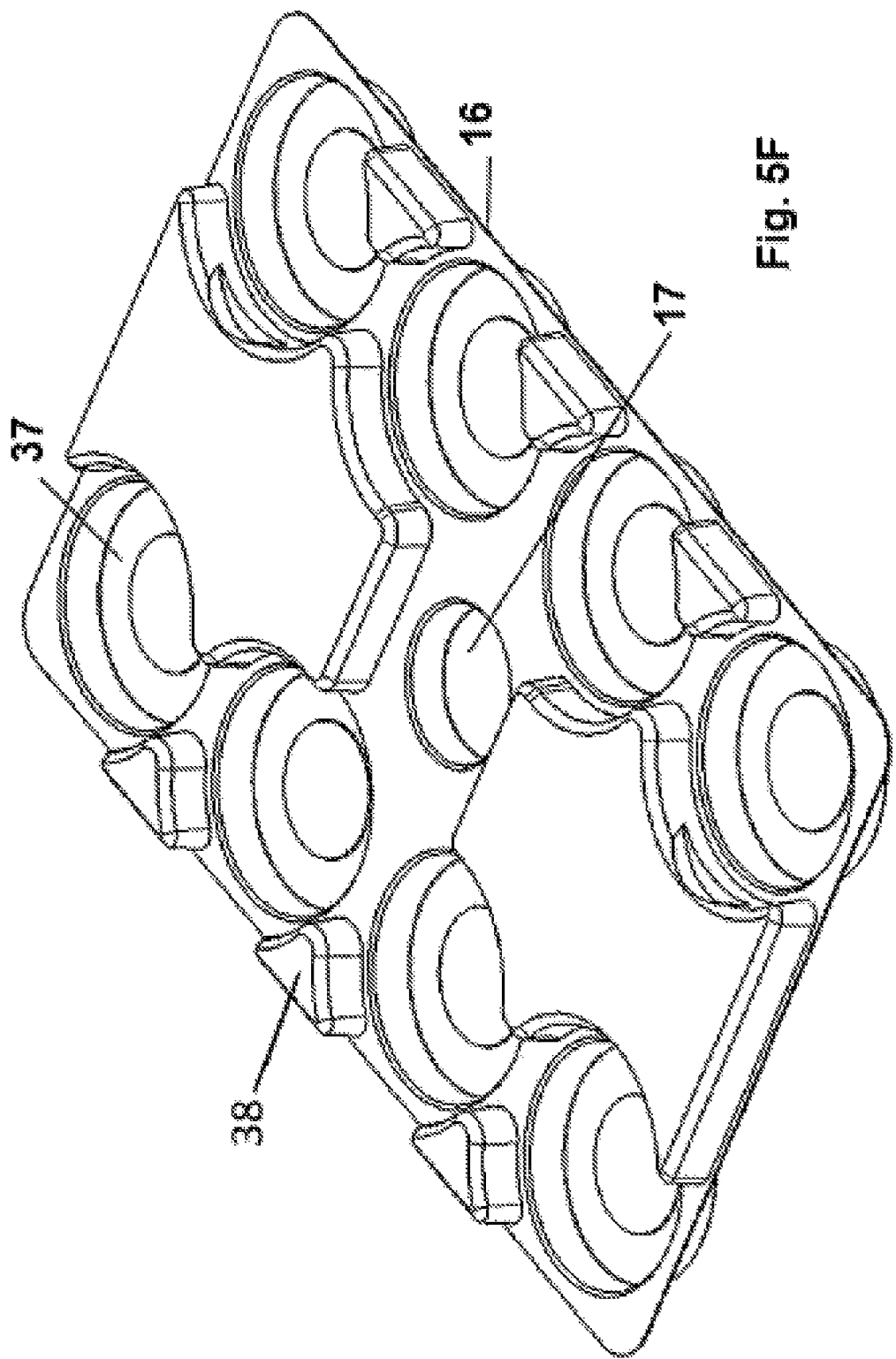

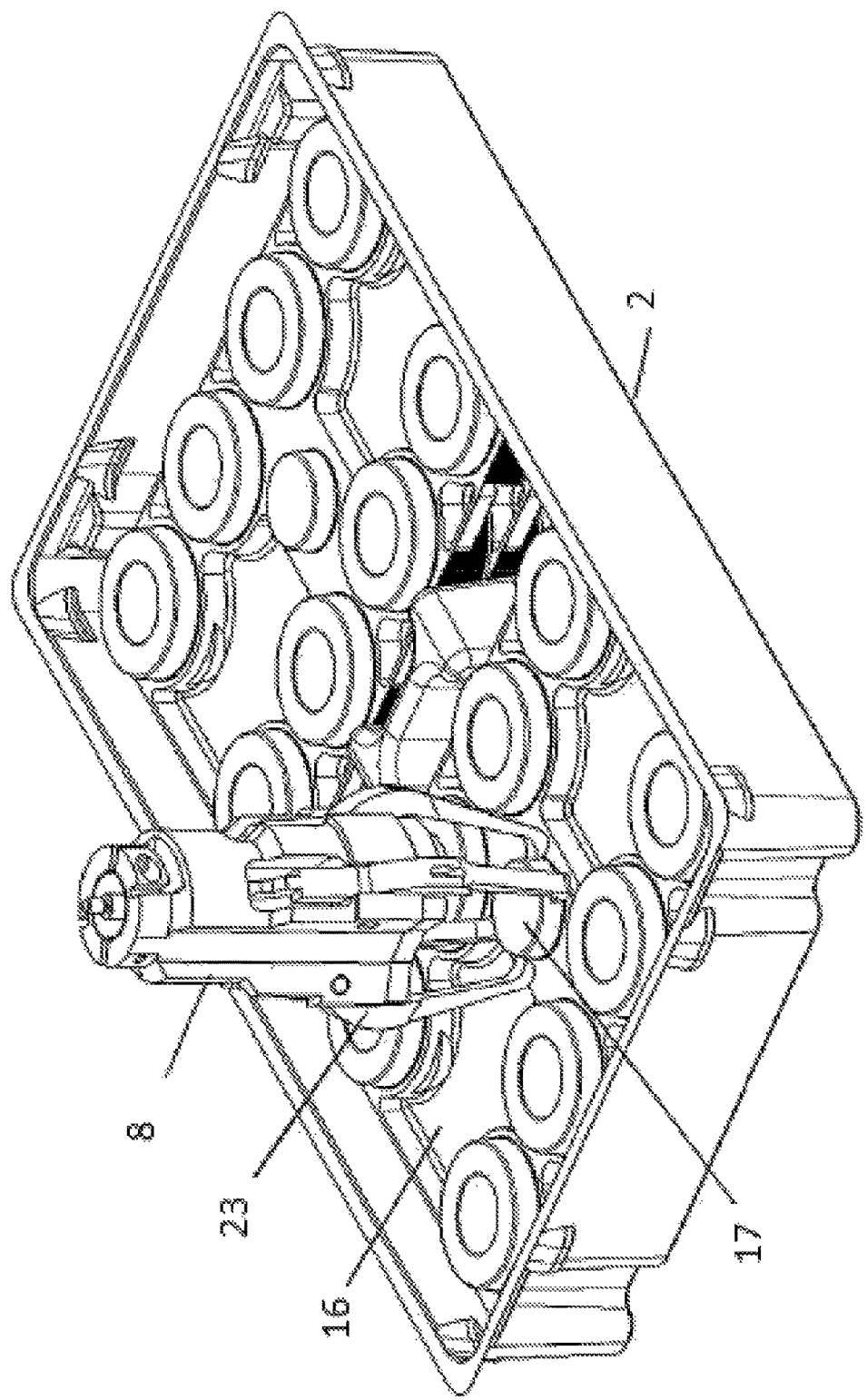

CAP SUPPLY FOR VESSELS CONTAINING BIOLOGICAL SAMPLES

CROSS-REFERENCES TO RELATED APPLICATIONS

The present application claims the benefit of priority under 35 U.S.C. § 119 of EP 13167057.2, filed May 8, 2013, the content of which is incorporated by reference herein in its entirety.

FIELD OF THE INVENTION

The present disclosure relates to the field of processing biological samples for analytical purposes, and in particular to a method for capping vessels containing biological samples. The disclosure also provides a cap supply for vessels containing biological samples, said cap supply comprising a plurality of caps in compartments in a predefined geometrical arrangement. The disclosure further provides a preanalytical system for capping vessels containing biological samples.

BACKGROUND OF THE INVENTION

The processing of biological material is of considerable significance for analytical purposes.

Automated analyzers are commonly used in such processes. Devices are commercially available which typically require test tubes or vials for biological samples and/or reagent liquids.

In order for the analyzer to conduct experiments on the biological sample, the cap typically needs to be removed prior to sample preparation or analysis, and equally importantly, the vessels have to be recapped, e.g., for transport to possible downstream processing units or for preservation of the sample.

Document U.S. Pat. No. 7,421,831 discloses a removable cartridge able to recap previously decapped vessels within an analyzer, the cartridge requiring a considerable extent of hardware inside the analyzer to fulfill its purpose.

The present disclosure provides a method, a preanalytical system and a cap supply for capping vessels containing biological samples, displaying several advantages.

SUMMARY OF THE INVENTION

In one embodiment, a method for capping vessels containing biological samples is provided. The method comprises providing a cap supply with a plurality of caps for the vessels within compartments in a predefined geometrical arrangement. The cap supply is introduced through an interface into a preanalytical system comprising a housing. For this purpose, it is reversibly docked to a feeder for inserting the cap supply into the preanalytical system and retrieving it therefrom. Subsequently, a cap is retrieved from the supply by a robotic manipulator, and transported to a workstation holding the vessels. A vessel is then capped using the manipulator. The steps from introducing the cap supply into the preanalytical system to capping a vessel are then repeated a certain number of times or until all caps of the supply have been retrieved. Finally, the cap supply is retrieved from the preanalytical system.

In another embodiment, a preanalytical system for capping vessels containing biological samples is provided. The system comprises a cap supply with a plurality of caps for the vessels within compartments in a predefined geometrical arrangement, a robotic manipulator for transporting the caps and capping the vessels, a programmable control unit for controlling the manipulator, and a workstation holding the vessels.

In another embodiment, a cap supply for providing caps for vessels containing biological samples is provided, the cap supply comprising a plurality of caps for the vessels, compartments accommodating the caps in a predefined geometrical arrangement.

BRIEF DESCRIPTION OF THE FIGURES

Other and further objects, features and advantages of the embodiments will appear more fully from the following description. The accompanying drawings, together with the general description given above and the detailed description given below, serve to explain the principles of the embodiments.

FIGS. 3A-F show perspective views of embodiments of a stackable cap supply (2) with compartments (12) accommodating caps (3) in a 6×8 arrangement. Interaction with a robotic manipulator (8), and empty/full as well as stacked cap supplies (2) are depicted.

FIGS. 4A-B show perspective views of variation of the cap supply (2) embodiment of FIG. 3 depicted without caps (3).

FIGS. 5A-G show perspective views of embodiments of a cap supply (2) with cradles (16) and compartments (12) accommodating caps in a 4×4 arrangement. The cap supply (2) and the cradles (16) are depicted with and without caps (3) and a removable lid (20), and interacting with a robotic manipulator (8).

DETAILED DESCRIPTION OF THE INVENTION

Figure 1:
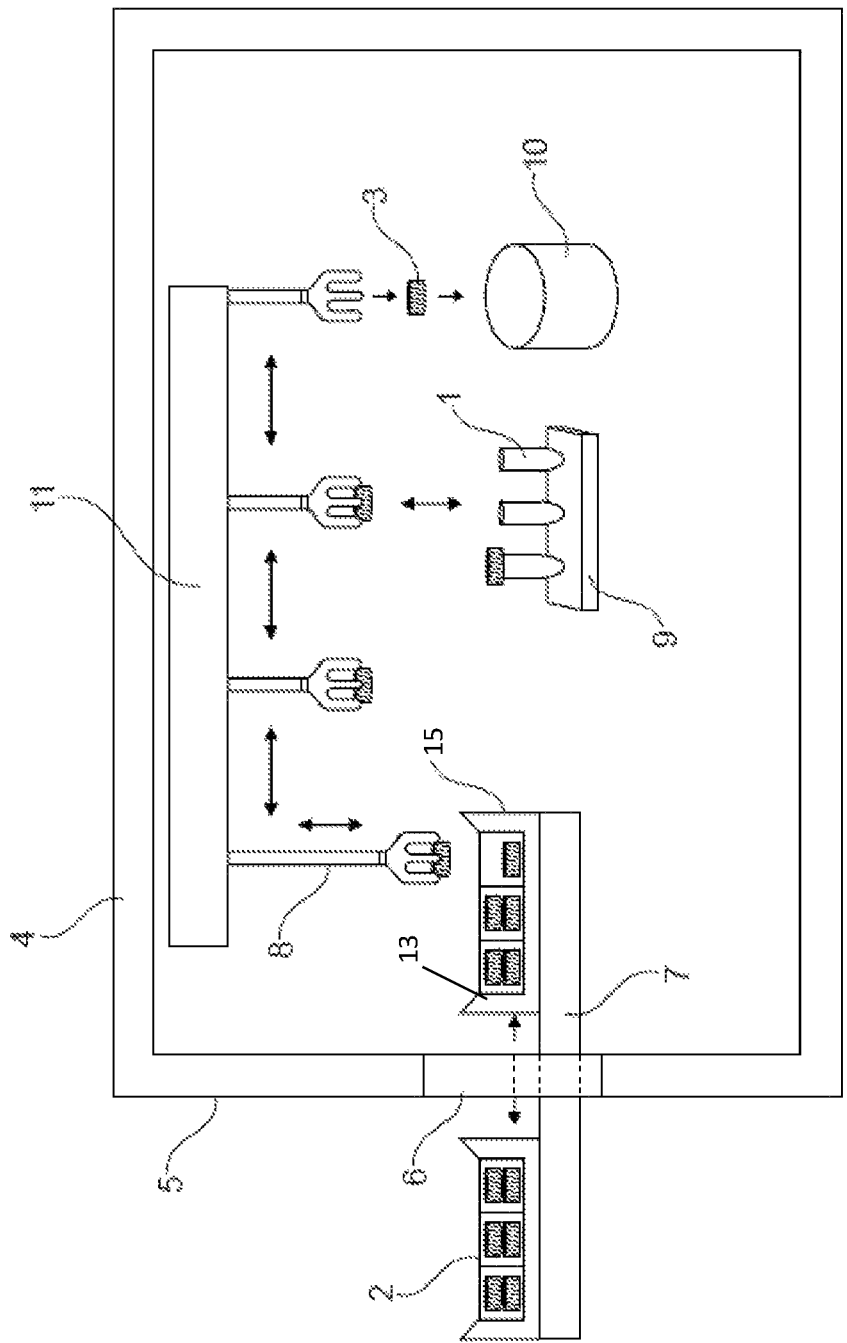
FIG. 1 shows a schematic view of a preanalytical system (4) including a cap supply (2) comprising caps (3).

By way of illustration, specific exemplary embodiments in which the invention may be practiced now are described.

In one embodiment, a method for capping vessels containing biological samples (1) is provided, the method comprising the steps of:

a) providing a cap supply (2) containing a plurality of caps (3) for the vessels containing biological samples (1), the cap supply (2) comprising compartments (12) accommodating the caps (3) in a predefined geometrical arrangement b) introducing the cap supply (2) into a preanalytical system (4) comprising a housing (5) through an interface (6) in said housing (5) by reversibly docking it to a feeder (7) for inserting the cap supply (2) into the preanalytical system (4) and retrieving it therefrom c) retrieving a cap (3) from the cap supply (2) with a laterally and vertically moveable robotic manipulator (8) and transporting it to a workstation (9) holding the vessels containing biological samples (1)

d) capping a vessel containing a biological sample (1) with the cap (3) using the laterally and vertically moveable robotic manipulator (8)

e) repeating steps b) to d) a number of times or until all caps (3) of the cap supply (2) have been retrieved by the laterally and vertically moveable robotic manipulator (8)

f) retrieving the cap supply (2) from the preanalytical system (4).

This method provides various advantages:

For instance, providing a disposable cap supply (2) to a preanalytical system (4) from which it can be retrieved again according to the herein-described method abolishes the need for additional dedicated hardware. In U.S. Pat. No. 7,421,831, the cartridge for capping and/or decapping interacts with a number of system components that are specifically constructed and arranged to facilitate the process of (de) capping. Among other structures, this document discloses an elevator including elevator tracks and load arms for the cartridge. The respective cartridge holder includes means for connecting a drive motor for activating cams comprised by the cartridge.

In contrast, the method described herein merely requires the presence of a robotic manipulator (8) that is in some embodiments also used for a variety of other tasks within the system. For example, the robotic manipulator (8) may also transport other components such as, e.g., the vessels containing biological samples (1), and/or components of the cap supply (2) such as cradles (16) separating different layers (41) of vessel caps (3).

Furthermore, the method described herein does not require any additional space ("footprint") for system components such as an elevator, a drive motor etc., thus rendering the respective preanalytical system more compact, economic and less complex.

In addition, a cap supply (2) as used in the method described herein need not exhibit a high level of complexity either, since the robotic manipulator (8) does not have to interact with the cap supply (2) itself in order to retrieve the caps (3).

Hence, the method described herein provides an easy and economical way of providing vessels with caps requiring a minimum amount of hardware, while the supply (2) may be made of inexpensive material. In some embodiments, the cap supply (2) is a disposable component, i.e., it is discarded after a number of uses. In some embodiments, it is a single-use component.

The terms "vessel" or "reaction vessel" comprise, but are not limited to, tubes, or the wells of plates such as microwell, deepwell or other types of multiwell plates. The outer limits or walls of such vessels are chemically inert such that they do not interfere with the reaction taking place within. Such reactions can comprise chemical or biochemical reactions such as, e.g., amplification of biological material such as nucleic acids, or binding reactions such as immobilization of a biological material on a solid support. In some embodiments, the vessels are tubes, also termed "sample tubes", which can be, e.g., sample collection test tubes, also called "primary tubes" used to receive a sample from a patient and to transport the sample contained therein to an analytical laboratory for diagnostic purposes, or "secondary tubes", which may be used to receive an aliquot of a sample from a primary tube.

The term "biological sample" refers to a material that may potentially contain an analyte of interest. The sample can be derived from any biological source, such as a physiological fluid, including blood, saliva, ocular lens fluid, cerebrospinal fluid, sweat, urine, milk, ascites fluid, mucous, synovial fluid, peritoneal fluid, amniotic fluid, tissue, cells or the like. The test sample can be pretreated prior to use, such as preparing plasma from blood, diluting viscous fluids, lysis or the like. Methods of treatment can involve filtration, distillation, concentration, inactivation of interfering components, and the addition of reagents. A biological sample may be used directly as obtained from the source or following a pretreatment to modify the character of the sample, e.g., after being diluted with another solution or after having been mixed with reagents, e.g., to carry out one or more diagnostic assays like, e.g., clinical chemistry assays, immunoassays, coagulation assays, nucleic acid testing, etc. In some embodiments, the biological sample is suspected to contain a certain nucleic acid.

A "cap supply", in the sense of the present subject matter, is a container comprising a plurality of caps (3) for vessels containing biological samples (1). The cap supply (2) is not limited to a specific shape or material, but in some embodiments contains the plurality of vessels (1) in a predetermined geometrical arrangement, as exemplified in the Figures of the present application. It can contain the caps (3) in one or more layers (41). Materials that the cap supply (2) can be made of comprise, e.g., plastics such as polypropylene (PP), polyethylene (PE), polyvinylchloride (PVC), polychlorotrifluoroethylene (PCTFE), cyclic olefin copolymers (COC) or polymers (COP), polyethylene terephthalate (PET), or the like. In some embodiments, the cap supply (2) is a blister pack, which is in some embodiments made by thermoforming or cold forming. In the case of thermoforming, a plastic film or sheet is unwound from the reel and guided though a preheating station on the blister line. The temperature of the pre-heating plates (upper and lower plates) is such that the plastic will soften and become pliable. The warm plastic will then arrive in a forming station where a large pressure (4 to 8 bar) will form the blister cavity into a negative mold. The mold is cooled such that the plastic becomes rigid again and maintains its shape when removed from the mold. In case of difficult shapes, the warm film will be physically pushed down partially into the cavity by a "plug-assist" feature. Plug-assist results in a blister cavity with more uniform wall distribution.

Regarding the dimensions of the cap supply (2), its height is at least the height of a cap (3), such that the caps (3) are enclosed by the cap supply (2) and need not be exposed to the surroundings until they are introduced into the preanalytical system (4) and retrieved by the robotic manipulator (8). In consequence, if the caps (3) are stacked to form multiple layers (41) in the cap supply (2), the cap supply's height is a least the height of the stacked caps (3).

The length and width of a cap supply (2) are at least according to the dimensions of one layer (41) of the plurality of caps (3) which they contain. For instance, in some embodiments the cap supply (2) contains caps (3) in a 6×8 matrix. Hence, in such embodiments the cap supply (2) has a width of at least 6 and a length of at least 8 juxtaposed caps (3). In some embodiments there needs to be some space in the compartments (12) around the caps (3). In those embodiments, in order to be able to retrieve the caps (3), the length and width of the cap supply (2) will typically exceed the minimum dimensions mentioned above.

The "compartments" of a cap supply (2) are its substructures comprising the caps (3). They are in some embodiments hollow cylinders separated by protuberances (18) of the cap supply material, such that the caps (3) can be stacked to form a column in the hollow cylinder compartment. In other embodiments, the compartments (12) are formed by sockets on which a cap (3) can be fixed such that it does not move within said cap supply (2), wherein in some embodiments other caps (3) can be stacked onto the lowermost cap which is placed on said socket. If the compartments (12) are hollow cylinders or other hollow geometrical forms accommodating the caps (3), then in some embodiments, e.g., if the robotic manipulator (8) is a robotic gripper, there is sufficient space (40) between the limits of the cylinder and the outer limits of the caps (3), such that the gripping parts (23) of the robotic gripper can enter this free space (40) and grip the caps (3).

The "predefined geometrical arrangement", in the context of this disclosure, is the structure in which the compartments (12) and thus the caps (3) contained therein are assembled. This structure allows the robotic manipulator (8) to locate the position in which a cap (3) is held without, e.g., requiring a sensor. However, such a sensor may also be included in the manipulator (8) within the scope of the subject matter. Without a predefined geometrical arrangement in the compartments (12), the caps (3) might also not be positioned at an appropriate angle for the robotic manipulator (8) to retrieve it from the cap supply (2). In some embodiments, the predefined geometrical arrangement comprises columns and rows which are in some embodiments arranged perpendicular to each other. Such arrangements are in some embodiments matrices of, e.g., 3×4, 4×4, 3×6, 4×6, 6×6, 6×8, 8×8, or other possible matrices.

The "caps", in the context of this disclosure, may be of different materials and may assume different shapes and colors, typically associated with the type of tube, i.e., the type of sample therein or the type of conditions the sample therein is subjected to or the type of process the tube and sample therein is going to be subjected to. In some embodiments, the caps (3) are screw caps and can thus be screwed onto and unscrewed from the respective vessels (1). In other embodiments, the caps (3) form a snap fit mechanism with the respective vessels (1). Other closing mechanisms are also possible in the context of the subject matter.

The action of closing a vessel (1) with a cap (3) is referred to as "capping", removing the cap (3) as "decapping". "Capping" means in some embodiments "reversibly closing", since often the capped vessels (1) need to be decapped again at some later point in time in order to access the biological sample contained therein, e.g., for analysis of the contents. As described above, the capping can be achieved using screw caps and thus involving a rotational movement, or it can involve exerting pressure to achieve a force fit, or the like.

A "preanalytical system" is an arrangement of components such as instruments interacting with each other with the ultimate aim to prepare a given sample for analysis. The preanalytical system may also comprise components for analysis, i.e., in such cases the prepared sample does not have to be delivered to a different system in order to be analyzed.

The preanalytical system (4) may comprise a "control unit" (CU). Such a control unit may be a separate unit or may be an integral part of an analytical instrument. The control unit controls the preanalytical system (4) in a way that the necessary steps for the assay protocols are conducted. That means the control unit, e.g., instructs the system to conduct certain pipetting steps to mix the sample with reagents, or to incubate the sample mixtures for a certain time, and the like. The control unit may receive information from a data management unit which test has to be done with a certain sample and based thereon determines the steps the preanalytical system (4) has to perform. In certain embodiments the control unit might be integral with the data management unit or may be embodied by a common hardware.

A "data management unit" comprising a test request database allows to relate a sample tube identification with the assays to be conducted with the sample contained in the vessel (1). The one or more analytical tests to be conducted with a particular sample are called a test request. The data management unit in many embodiments is connected to a LIS (laboratory information system) and/or a HIS (hospital information system). The data management unit (DMU) can be a unit within or co-located with a preanalytical system (4), e.g., it can be part of the control unit. Alternatively the DMU can be a unit remotely located from the preanalytical system (4), e.g., can be embodied in a computer connected via a network to the preanalytical system (4).

In the context of the present subject matter, the preanalytical system (4) comprises a "housing", which at least partially encloses the system components of the preanalytical system (4). In some embodiments, the housing (5) completely encloses the system components. The housing (5) separates the system components from the outside and thus, e.g., from potential sources of contamination, possibly leading to false analytical results. On the other hand, biological material such as, e.g., clinical sample often contain infectious agents, such that the housing (5) also reduces the risk of infection of the technical personnel with such material. The housing (5) can be made of a variety of materials including, e.g., metal and/or plastic. It can be transparent or non-transparent, or it can comprise transparent elements such as, e.g., a window allowing a person to visually monitor certain processes within the preanalytical system (4) from the outside. As set out above, the preanalytical system may also comprise analytical components. Performing both preanalytical preparation and analysis of the prepared sample within the same housing minimizes exposure of potentially infectious sample material and/or material that is sensitive to contamination and facilitates the workflow.

The "interface" in the housing (5) is a gate that permits physical communication between the inside and the outside of the preanalytical system (4). In some embodiments, the interface (6) comprises a lid that can be manually or automatically opened and closed in order to transfer components or samples in- and outside of the preanalytical system (4).

A "feeder" is a part of the interface (6) described supra. It facilitates the automatic or manual transfer of the cap supply (2) through the interface (6) from the outside to the inside of the preanalytical system (4), and also its retrieval in the opposite direction. In some embodiments it is a moving part such as, e.g., a drawer, or a robotic arm, or a suspension.

"Reversibly docking" in the sense of the subject matter means attaching objects to each other with the possibility of subsequent or later undocking. For instance, the cap supply (2) can be reversibly docked to the feeder (7) by any suitable mechanism such as, e.g., latches, force fit (e.g., by friction/sticky surfaces), form fit (e.g., bolting, bayonet coupling, snap fitting, an undercut in the casting), hook-and-loop fastening, pressure (e.g., exerted manually or by a robotic arm, or applying a vacuum), magnetism, or other means. The cap supply (2) can be reversibly docked to the feeder (7) either directly or indirectly. "Reversibly docking" implies that the undocking can be easily carried out without destroying or damaging any of the involved objects.

In some embodiments, the cap supply (2) comprises a "mount" which is a structure facilitating physical interaction between the cap supply (2) and certain components of the preanalytical system (4) such as, e.g., the feeder (7). More specifically, in some embodiments involving a mount (13), the latter may facilitate the reversible docking of the cap supply (2) to the feeder (7). In other embodiments, the mount (13) may be used to attach the cap supply (2) to a holder within the preanalytical system (4) such that the supply (2) is fixed in z- and/or x/y-direction while the caps (3) are retrieved by the robotic manipulator (8). In some embodiments, the feeder (7) itself serves as such a holder.

Hence, an embodiment is the method described herein, wherein the cap supply (2) comprises a mount (13).

A "laterally and vertically moveable robotic manipulator" is a robotic component that handles other components of the preanalytical system (4) and/or disposable components that are used within the preanalytical system (4). It can be moved laterally (along an x- and or y-axis) and vertically (along a z-axis). In some embodiments, the manipulator (8) can be moved within a part or all of the preanalytical system (4). In order to be moveable, the manipulator (8) can, e.g., be flexibly suspended and/or comprise a flexible robotic arm. For instance, the lateral movement can be facilitated by a rotatable robotic arm fixed, e.g., to the bottom or the ceiling of the housing (5) of the preanalytical system (4). Vertical movement can, e.g., be achieved by a telescope arm. Also, the manipulator (8) can comprise a bipartite robotic arm rotatable at its base, e.g., at the bottom of the preanalytical system (4), wherein the two parts of the arm are attached to each other via a hinge or another type of joint. By combined movement of the hinge and rotation of the arm at its base, the robotic manipulator (8) may be movable in all directions. In order to handle material such as other system components or disposable materials such as vessels or caps, it can comprise, e.g., gripper arms (23). In such embodiments, the robotic manipulator (8) is a gripper. Alternatively or additionally, the manipulator (8) can comprise means to apply a vacuum or at least negative pressure. Such a structure can for instance be or comprise a vacuum cup.

In some embodiments, more than one laterally and vertically moveable robotic manipulator (8) is used. For instance, two, three or four robotic manipulators (8) may act simultaneously or at different times within the preanalytical system (4). In one embodiment, two robotic manipulators (8) retrieve caps (3) from the cap supply (2) simultaneously, wherein in one embodiment there is at least one cap (3) in the cap supply (2) in between the two caps (3) that are simultaneously retrieved from their respective compartments (12) by the robotic manipulator (8).

A "workstation" is a component of the preanalytical system (4) where certain steps are carried out such as, e.g., pipetting, mixing, heating/cooling, magnetic manipulation, or the like. Thus, the workstation (9) can comprise, e.g., heating/cooling elements such as, e.g., Peltier elements, or magnets, or the like. In the context of the method described herein, the workstation (9) holds the vessels containing biological samples (1). For this purpose, the workstation (9) can, e.g., comprise a rack or a different kind of holder for the vessels (1).

Before or after capping vessels containing biological samples (1), they often need to be decapped in order to access the biological sample, e.g., for the purpose of analysis or other manipulation. For instance, decapping of the vessels (1) can occur for pre-analytic preparation of a biological sample. Subsequently, the prepared sample may be capped again in order to safely transport the sample inside the vessel to either a different place within the preanalytical system (4) or, e.g., to an analytical system, where analysis of the biological sample is carried out, such as, e.g., amplification in the case of nucleic acid analysis.

Hence, an embodiment is the method described herein, additionally comprising the step of decapping one or more of the vessels containing biological samples (1) using the laterally and vertically moveable robotic manipulator (8).

As described above the decapping is carried out by the same robotic manipulator (8) such that no further components are required that may render the system more complex and voluminous.

In some embodiments of the method described herein, the method further comprises discarding the respective one or more caps (3) into a waste container (10) comprised by the preanalytical system (4).

As mentioned above, the robotic manipulator (8) may be a gripper. In such embodiments, there is sufficient space (40) within the compartments (12) around the caps (3), such that the gripping parts (23) of the robotic gripper can enter this free space (40) and grip the caps (3).

Thus, an embodiment is the method described herein, wherein the laterally and vertically moveable robotic manipulator (8) is a gripper, and wherein the compartments (12) of the cap supply (2) comprise free space (40) around each cap (3) sufficient for the gripper to retrieve the caps (3) from the compartment (12).

A robotic gripper bears the advantage that any components it is supposed to handle need not exhibit specific structural features for interaction with said gripper, as opposed, e.g., to cases where a hook comprised by the manipulator (8) needs an eye or equivalent feature on the component to be handled. The gripper is in some embodiments flexible with regard to size and shape of the components to be handled.

In order to provide a relatively large number of caps (3) to the preanalytical system (4) at a time, the caps (3) in the cap supply (2) in the method described herein are stacked to form a plurality of layers (41).

In such embodiments, the caps (3) can, e.g., have an appropriate shape such that a plurality of them can be directly stacked onto one another, or there can, e.g., be separation layers such as sheets or cradles (16) between the layers (41) of caps (3). Other possibilities for stacking caps (3) are known to the person skilled in the art.

In case the vessels (1) are closed with screw caps or similar closures, the laterally and vertically moveable robotic manipulator (8) needs to perform also rotational movements to screw or unscrew the respective caps (3). Hence, another embodiment is the method described herein, wherein the capping of the vessel containing a biological sample (1) in step d) is performed by rotational movement of the laterally and vertically moveable robotic manipulator (8).

Also an embodiment is the method described herein, wherein the laterally and vertically moveable robotic manipulator (8) is controlled by a programmable control unit (11).

The "programmable control unit" is a component steering the robotic manipulator (8). It may be the same control unit as the one described supra in the context of the preanalytical system (4), or a different control unit. With respect to the robotic manipulator (8), the programmable control unit (11) takes into account the position of, e.g., caps (3) and vessels (1) and in some embodiments other components, and controls the movements of the manipulator (8) accordingly. For instance, the control unit (11) may be programmed in a way that the caps (3) are picked up from their compartments in the cap supply (2) at a specific position, and are then transported to the vessels (1) in the workstation (9). In case the caps (3) are screw caps, the control unit (11) can be programmed to rotate the manipulator (8) in order to cap the vessels (1). As described above, the control unit (11) may receive information from or via a data management unit. For instance, the cap supply (2) can contain an identification tag (14), such as a barcode or RFID (Radio-Frequency Identification) tag or the like. The information contained therein may be processed by the data management unit and transmitted to the programmable control unit (11), which, e.g., initiates said rotational movement if it received the information that the cap (3) is a screw cap. Also, if the robotic manipulator (8) is, e.g., a gripper, information about the size and shape of vessels (1) and caps (3) can be taken into account by the programmable control unit (11) when performing the gripping movement with the gripper arms (23).

Another embodiment relates to a preanalytical system (4) for capping vessels containing biological samples (1), the preanalytical system (4) comprising:

a cap supply (2) containing a plurality of caps (3) for the vessels containing biological samples (1), the cap supply (2) comprising compartments (12) accommodating the caps (3) in a predefined geometrical arrangement a housing (5) at least partially enclosing the components of the preanalytical system (4), said housing (5) comprising an interface (6) comprising a feeder (7) for inserting the cap supply (2) into the preanalytical system (4) and retrieving it therefrom (7)

a laterally and vertically moveable robotic manipulator (8) for transporting the caps (3) within the preanalytical system (4) and for capping the vessels containing biological samples (1) with the caps (3)

a programmable control unit (11) for controlling the laterally and vertically moveable robotic manipulator (8)

a workstation (9) holding the vessels containing biological samples (1).

As described above, "partially enclosing" in the context of the housing (5) means the separation and possibly protection of the inside of the preanalytical system (4) with its components from the outside and vice versa, thus preventing contamination of the analytical components as well as loss of containment of infectious sample material. In some embodiments, the housing (5) completely encloses the components of the preanalytical system (4), such that the interface (6) is the only possibility for the cap supply (2) to be transported in and out of the preanalytical system (4).

In some embodiments, the cap supply (2) comprises a mount (13).

In some embodiments, the preanalytical system (4) described herein additionally comprises a waste container (10) for collecting disposed caps.

It is one of the advantages of the present subject matter that the cap supply (2) is retrieved from the system (4) after usage. Thus, the waste container (10) or possibly other components within the system (4) need not collect the used cap supply or supplies (2), which may require a considerable amount of space within the preanalytical system (4) and may lead to a situation where the waste container (10) needs to be exchanged frequently. If only disposed caps are collected in the waste container (10), those exchange intervals can be significantly larger. In some embodiments, the waste container also collects cradles (16) removed from the respective cap supply (2). Such cradles for separating distinct layers (41) of caps (3) within the supply (2) likewise require significantly less space than an entire cap supply (2).

In some embodiments of the preanalytical system (4) described herein, the laterally and vertically moveable robotic manipulator (8) is a gripper, wherein the compartments (12) of the cap supply (2) comprise free space (40) around each cap (3) sufficient for the gripper to retrieve the caps (3) from the compartment (12).

As set out above, the programmable control unit (11) is in some embodiments programmed according to an identification tag (14) comprised by the cap supply (2). In some embodiments, the identification tag (14) is a barcode, in other embodiments it is an RFID tag.

Such identification tags (14) can enhance the level of automation of the preanalytical system (4) by providing the system (4) with information (such as, e.g., size, shape, number, and/or position of the caps (3)) which thus need not be introduced by the operating person. As described above, once the cap supply (2) is loaded onto the system (4) via the interface (6) comprising the feeder (7), these embodiments confer the advantage of reduced hands-on time required for conducting the analytical or pre-analytical steps on the preanalytical system (4).

In order to enhance the interaction between feeder and cap supply, in some embodiments of the preanalytical system described herein the feeder (7) comprises a holder (15) for the mount (13) comprised by the cap supply (2).

Such a holder (15) can, e.g., comprise or be a hook, or a latch, or a plug, or a comparable mechanism known to the person of skill in the art. The holder (15) physically interacts with the mount (13) comprised by the cap supply (2). In some embodiments, the holder (15) is or comprises a recess such as, e.g., an eye whereas the mount (13) is or comprises a hook, or vice versa. In other embodiments, the rim of, e.g., the upper or lower side of the cap supply (2) is formed as or comprises a collar (25) or other type of projection, which can be held by a bracket comprised by the feeder (7). Alternatively, the feeder (7) may comprise a cavity as a holder for receiving the bottom of the cap supply (2) which in such case would be shaped to fit into said cavity, thereby acting as a mount (13).

In an embodiment of the preanalytical system (4) described herein, the feeder (7) for inserting the cap supply (2) into the preanalytical system (4) and retrieving it therefrom is a drawer.

In another embodiment of the preanalytical system (4) described herein, the laterally and vertically moveable robotic manipulator (8) is capable of a rotational movement around its longitudinal axis.

The "longitudinal axis" is herein the axis perpendicular to the cap (3). For instance, when the cap (3) is a screw cap, then the manipulator (8) performs a rotational movement leading to opening or closing of the respective screw cap. Thus, in some embodiments of the preanalytical system (4) described herein, the rotational movement along the longitudinal axis is a rotational movement for screwing or unscrewing screw caps.

Another embodiment is a cap supply (2) for providing caps (3) for vessels containing biological samples (1), comprising:

a) a plurality of caps (3) for vessels containing biological samples (1)

b) compartments (12) accommodating the caps (3) in a predefined geometrical arrangement.

As set out above, such a cap supply (2) allows a quick, easy and inexpensive provision of caps (3) to a preanalytical system (4) with the objective of capping vessels containing biological samples (1). The predetermined geometrical arrangement allows for an ordered retrieval of the caps (3) from the supply (2) with a robotic manipulator (8).

In some embodiments, the cap supply (2) further comprises a mount (13).

As described herein, the mount (13) facilitates physical interaction of the cap supply (2) with components of a preanalytical system. In some embodiments, it facilitates interaction with a feeder (7) of a preanalytical system (4) for transporting the cap supply (2) in- and outside of the system (4).

In some embodiments of the cap supply (2) described herein, the compartments (12) comprise free space (40) around each cap (3) sufficient for a laterally and vertically moveable robotic gripper (8) to retrieve the caps (3) from the compartment (12).

Also, in some embodiments the caps (3) are stacked in the compartments (12) to form a plurality of layers (41). In such embodiments, larger number of caps (3) can be brought into the preanalytical system (4) with one cap supply (2).

In some embodiments, the layers (41) of said plurality are separated by cradles (16). In this context, "cradles" are separation layers between the layers (41) of caps (3). Such cradles (16) can facilitate the stacking of the plurality of layers (41), e.g., in case the caps (3) are not per se easily and stably stackable on one another. The cradles (16) can be dimensioned essentially according to the entire breadth and length of the cap supply (2) such that they separate the complete layers (41) of caps (3) from each other, or the cradles (16) can separate parts of them. For instance, in a 4×4 geometrical arrangement of the compartments (12) and thus caps (3), one cradle (16) may separate half of the cap layers (41) (4×2 or 2×4), and a second cradle (16) the other half accordingly. As soon as one layer (41), or half a layer (41) or another part separated by a cradle (16) has been retrieved from the cap supply (2), the respective cradle (16) is removed from the cap supply (2) such that the robotic manipulator (8) can access the next layer (41) or part of a layer (41) of caps (3).

In some embodiments, the cradles (16) are handled by a robotic manipulator (8), which allows the preanalytical system (4) that the cap supply (2) is used in to work without adding considerable complexity to the system (4) due to the cradles (16), since no additional specifically dedicated hardware components are required.

In some embodiments, the cradles (16) comprise knobs (17) for interaction with the laterally and vertically moveable robotic manipulator (8).

Such knobs (17) are especially useful when the robotic manipulator (8) is a gripper, since the knobs (17) provide a contact surface for the gripping parts (23).

As set out above, the cap supply (2) is in some embodiments made of plastics, and in some embodiments it is a blister pack.

In embodiments where the cap supply (2) is made of plastics, and especially where it is a blister pack, it can be produced on large scales in an efficient and inexpensive manner, such that such cap supplies (2) can be readily used as disposables. Also, protuberances (18) as mentioned above can be especially easily formed during the production process of a blister pack.

In the context of the disclosure, "disposable" means a component which is used only a limited number of times, in some embodiments only once, and is then discarded. In the context of the disclosure, the cap supply (2) is in some embodiments disposable. Hence, it can be used according to the method described herein, and after retrieval from the preanalytical system (4) it can be discarded. A disposable cap supply (2) can be provided to the personnel operating a preanalytical system (4), such that they need not, e.g., refill once-retrieved cap supplies (2) with fresh caps (3).

The compartments (12) of the cap supply described herein are in some embodiments separated by protuberances (18) extending from the bottom of the cap supply (2).

In some embodiments, the compartments (12) are columns which are in some embodiments cylindrical.

In further embodiments, the bottom of each compartment (12) comprises a protuberance (19) for supporting a cap (3), said protuberance (19) in some embodiments being a socket, in other embodiments a recess. In this context, a convex protuberance (19) supports the caps (3) or the lowermost cap (in the case of multiple layers (41)) by functioning as a socket on which the cap (3) is placed to prevent undesired lateral movement of the cap (3) within the cap supply (2). A concave protuberance (19) achieves the same by providing a recess in which the cap (3) is enclosed at least with a part of its total height.

In order to close the cap supply (2) and separate and protect its contents from the surroundings, the cap supply (2) in some embodiments comprises a removable lid (20). The lid (20) may be removed before use, e.g., by the operating person, or automatically by the robotic manipulator (8), or the like.

In some embodiments, the cap supply (2) is stackable, which is in some embodiments achieved through projections and recesses comprised by the cap supply (2), wherein the projections fit the recesses such that the cap supplies (2) can be stacked on one another.

In embodiments where multiple cap supplies (2) are stackable, they may be more easily and efficiently shipped, e.g., to laboratories with preanalytical systems (4). For instance, a stack of two or more cap supplies (2) can be packaged together, e.g., by wrapping them with plastic foil or other suitable materials as a stack. Such packaging can, e.g., removed by the operating personnel prior to loading the cap supply or supplies (2) onto the system (4). In some embodiments, the stacks are disassembled manually or automatically in order to load the single cap supplies (2) onto the system (4).

It is to be understood that specific embodiments described either for the method, the preanalytical system or the cap supply mentioned herein also apply to the respective other categories.

The following non-limiting examples illustrate certain embodiments of the present subject matter.

EXAMPLES

In the following, examples are provided in order to display certain embodiments and to exemplify the method, preanalytical system (4) and cap supply (2) described herein. It is to be understood that also other embodiments are comprised by the scope of the subject matter, as known by the person skilled in the art.

FIG. 1 provides a general schematic overview of the preanalytical system (4) described herein. A cap supply (2) comprising caps (3) accommodated by respective compartments (12) in stacks of two is transferred from the outside (left position) to the inside (right position) of the preanalytical system (4) through the interface (6) of the housing (5). For this purpose, it is reversibly docked via a mount (13) to the holder (15) of a feeder (7) comprised by the interface (6). Inside the preanalytical system (4), a laterally and vertically moveable robotic manipulator (8) depicted as a robotic gripper is extended via a moving arm such as, e.g., a telescope arm (see vertical double-headed arrow) to reach for a cap (3) in the cap supply (2), grips it and retrieves it therefrom. In the following, the robotic manipulator (8) holding the cap (3) is shortened via its arm (see vertical double-headed arrow) and moved laterally (see horizontal double-headed arrows) to a workstation (9) holding vessels containing biological samples (1). The moving arm is then re-extended (see vertical double-headed arrow) such that the robotic manipulator (8) reaches a vessel (1) in the workstation (9) and caps it with the respective cap (3). On the right-hand side, it is further depicted how the robotic manipulator (8) decaps a vessel (1), retrieves the cap (3) and transports it by lateral movement (see horizontal double headed arrow) to a waste container (10), where the cap (3) is disposed (see vertical arrows pointing down). The robotic manipulator (8) is controlled by a programmable control unit (11).

After a number of times or when all caps (3) of the cap supply (2) have been retrieved by the laterally and vertically moveable robotic manipulator (8), the cap supply (2) is retrieved via the feeder (7) through the interface (6) from the preanalytical system (4).

Figure 2A:
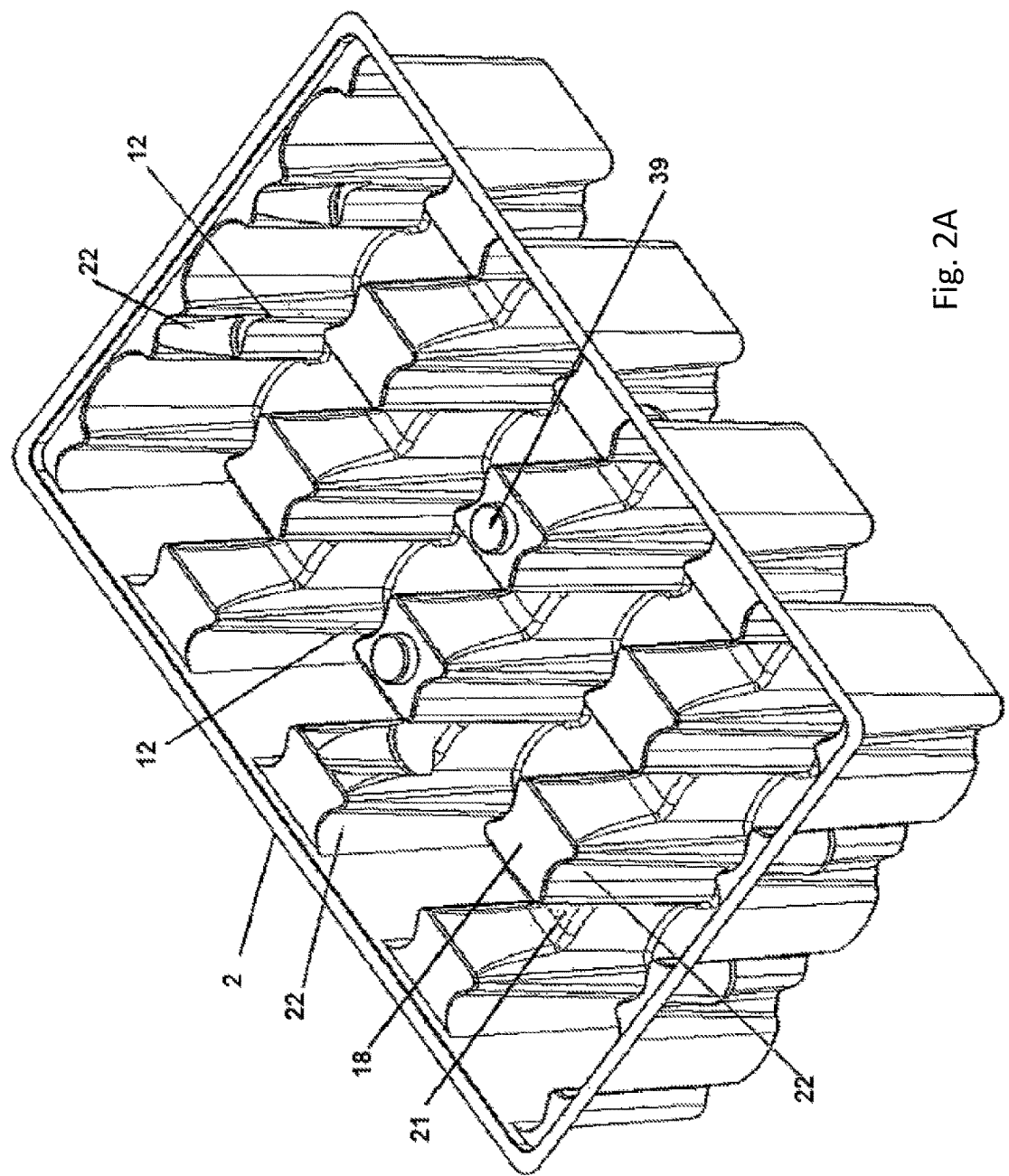
FIGS. 2A-E shows perspective views of embodiments of a cap supply (2) with compartments (12) accommodating caps (3) in a 4×3 arrangement. The cap supply (2) is depicted with and without caps (3) and a removable lid (20), and interacting with a feeder (7) as well as a robotic manipulator (8).

The cap supply (2) shown in FIG. 2A (perspective view from above) is depicted in an empty state such that the inside of the compartments (12) arranged in a 4×3 matrix can be seen. The compartments (12) in this embodiment are separated from one another by protuberances (18) extending from the bottom of the cap supply (2). The arrangement shown here comprises four interconnected protuberances between each of the four columns of compartments (12), wherein the protuberances (18) extending from bottom to top are interconnected via lower protuberances (21) contributing to stability and ease of manufacturing of the cap supply (2). The knobs (39) on the two central protuberances (18) may serve as sites for attaching a foil to the cap supply (2) for sealing, e.g., by welding. The recesses (22) extending along the vertical axis of the protuberances (18) facilitate the entry of the arms (23) of a robotic gripper.

Figure 2B:
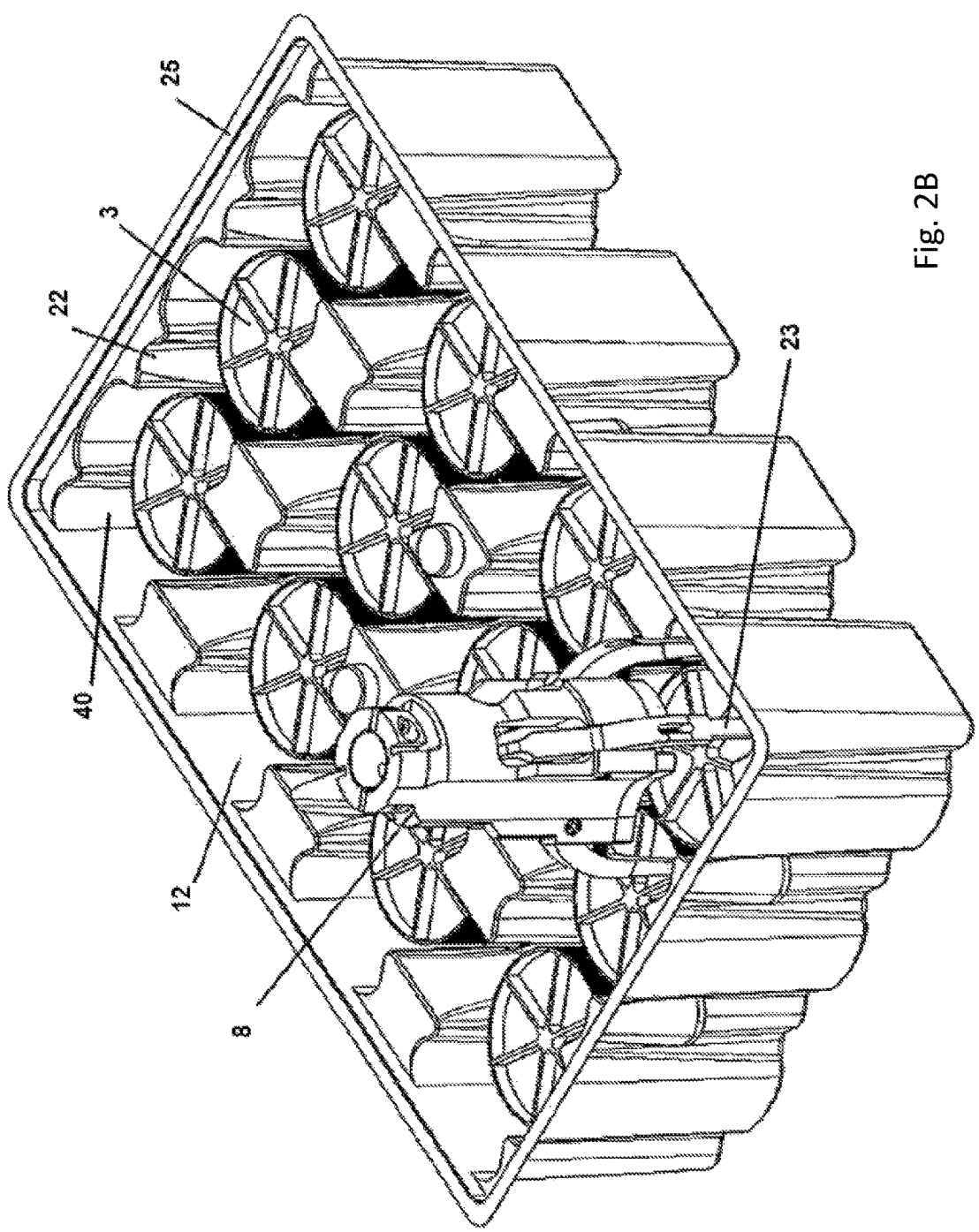
Figure 2C:
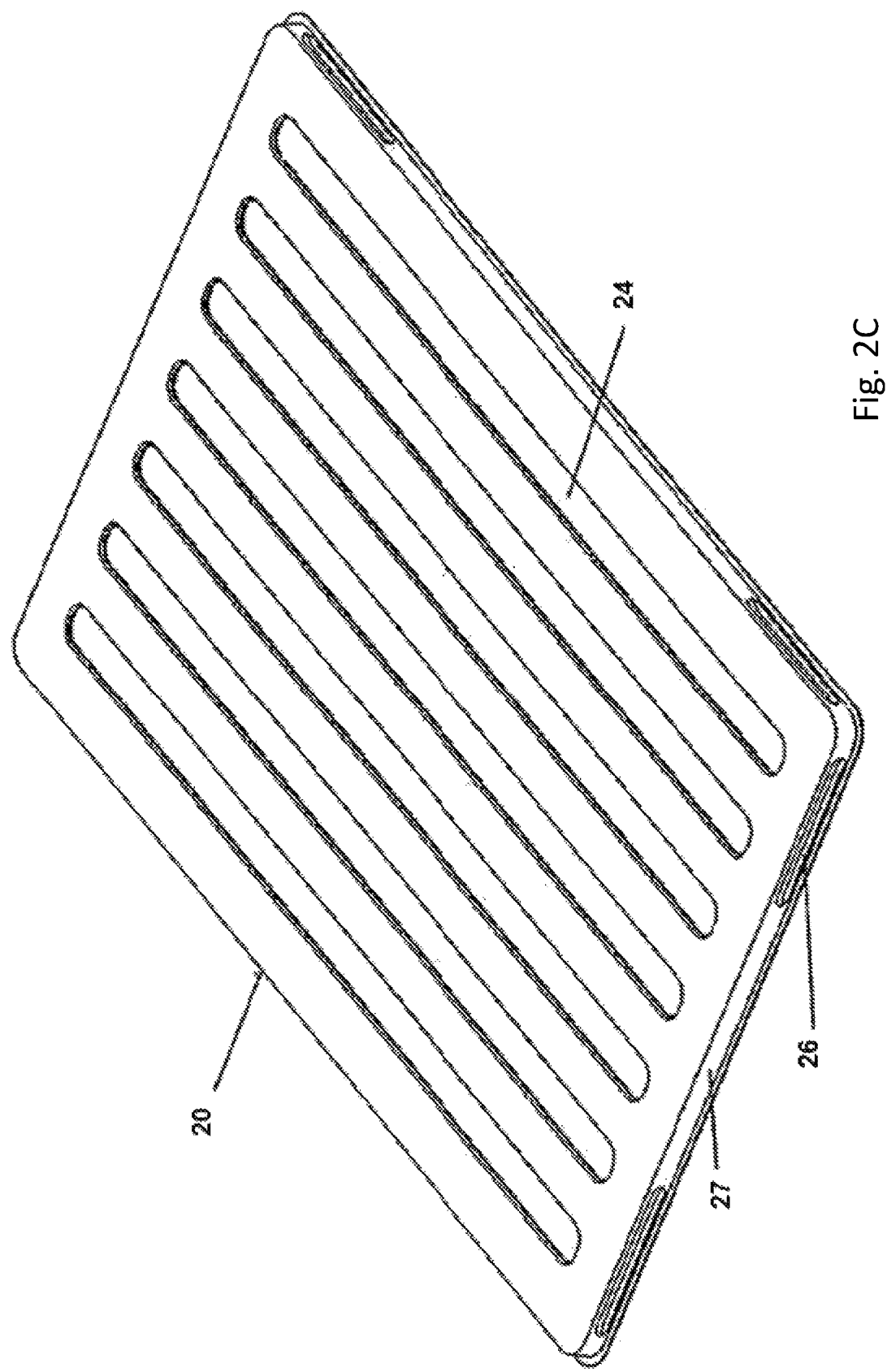
Figure 2D:
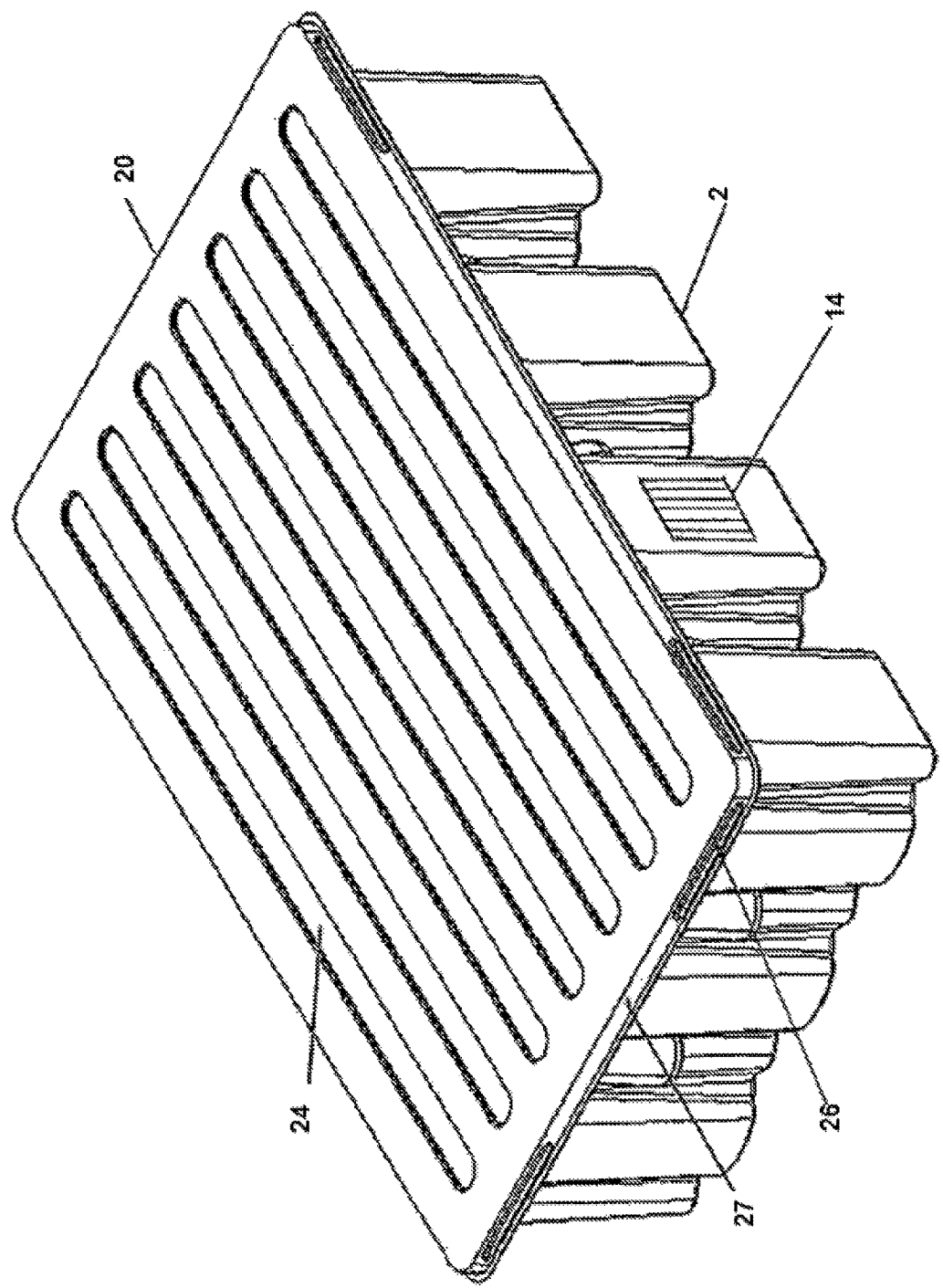

The latter can be seen in FIG. 2B, providing a perspective view from above of the cap supply (2) described supra. The gripper arms (23) of the robotic manipulator (8), in this embodiment a robotic gripper, are placed around a cap (3) using the free space (40) provided by the recesses (22) extending along the vertical axis of the separating protuberances (18). Only the gripping part of the robotic manipulator (8) is displayed for the sake of clarity, while those parts conferring lateral and vertical movability are not depicted. The caps (3) in the compartments (12) are stacked on one another to form multiple layers (41), while only the top layer is visible in the current depiction. Further visible is a collar (25) around the upper rim of the cap supply (2) for interaction with the removable lid (20) shown in FIG. 2C from above (perspective view). The protrusions (26) extending from the outer to the inner side of the overhang (27) engage the collar (25) of the cap supply's main body in order to close the cap supply (2) via snap fit, as shown in a perspective view from above in FIG. 2D. The grooves (24) along the lid (20) contribute to its mechanical stability. Also visible is an identification tag (14), in this embodiment a barcode, attached to the outer side wall of the cap supply (2).

Figure 2E:
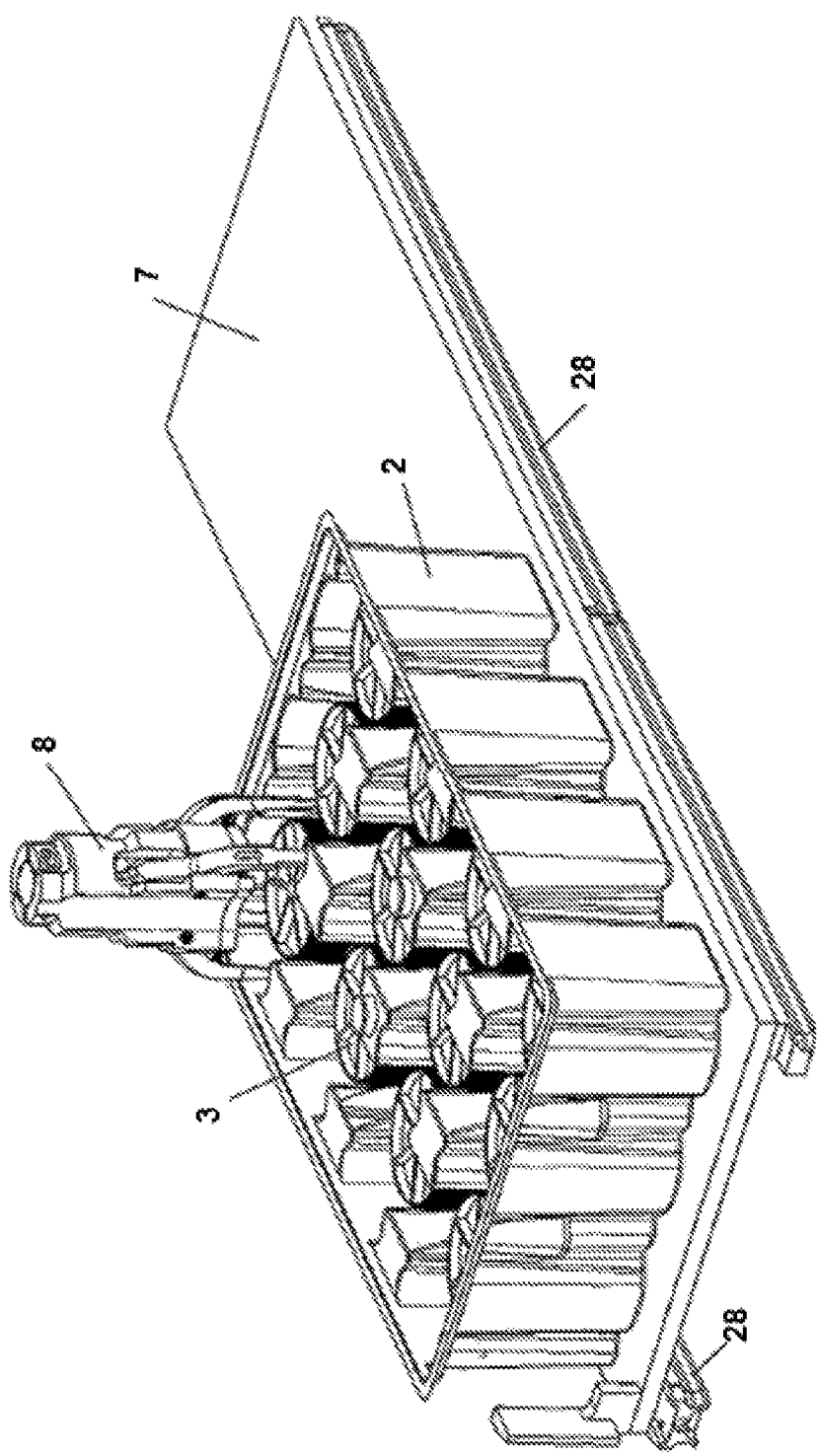

An open cap supply (2), again in a perspective view from above, is shown in FIG. 2E while placed on a feeder (7) and interacting with a robotic manipulator (8) which is retrieving a cap (3). In this embodiment, the feeder (7) is shown as a drawer comprising a pair of guiding rails (28) for interaction with the interface (6) of the housing (5) of the preanalytical system (4). Since the robotic manipulator (8) is gripping a cap (3), it can be seen that the position of the cap supply (2) on the feeder (7) is within the preanalytical system (4). At the end of the process, the feeder (7) will transport the used cap supply (2) outside the preanalytical system (4).

In the embodiment shown in FIGS. 3A-F, a cap supply (2) comprises compartments (12) accommodating caps (3) in an 8×6 arrangement. The caps (3) in the cap supply (2) shown in FIG. 3A from above in a perspective view form one layer and sit on sockets formed by protuberances (19) extending from the bottom of the cap supply (2). The cap supply's lower rim is surrounded by a collar (29) which can facilitate stacking or interact—as a mount—with a suitable structure of the feeder (7). The protrusions (30) at the lower rim can, e.g., contribute to better stacking properties during production of the cap supply (2), or they can also serve to interact with the feeder (7). Retrieval of a cap (3) from a compartment (12) by a laterally and vertically moveable robotic manipulator (8)—in this embodiment depicted as a robotic gripper—can be seen in FIG. 3B. The neighboring caps (3) do not interfere with the four gripper arms (23), because the caps (3) are sufficiently spatially separated from one another.

Figure 3A:
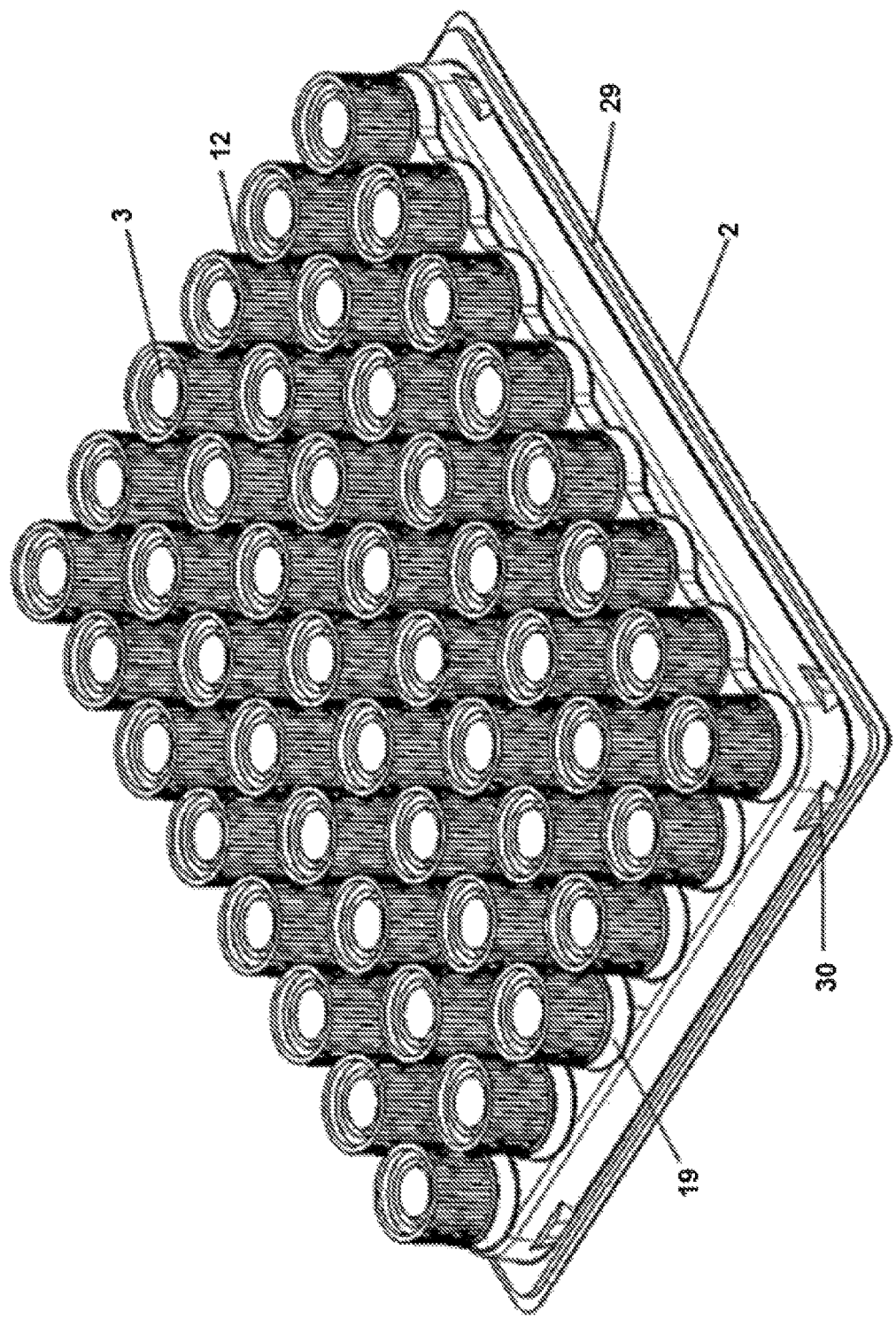
Figure 3C:
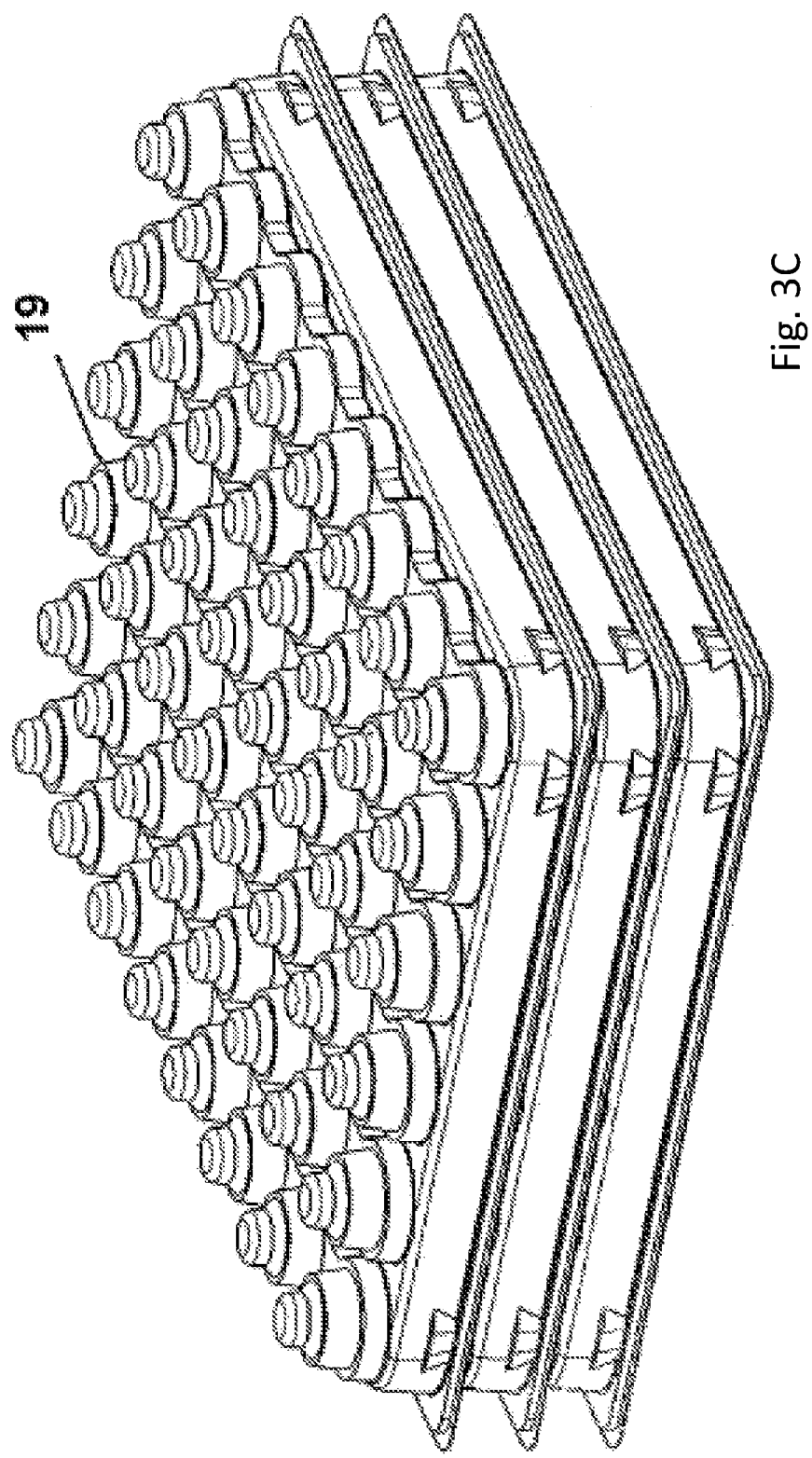

FIG. 3C depicts a stack of three cap supplies (2) viewed from diagonally above. The topmost cap supply (2) does not contain any caps, such that the protuberances (19) serving as sockets for the caps (3) are visible. The single empty cap supply (2) as shown in FIG. 3D provides a clearer depiction of those protuberances (19) which in this embodiment show an integral tripartite structure: a foot (31) onto which the lower rim of the cap (3) is placed, an intermediate ring (32) engaging the lateral inner surface of the cap (3), and a top knob (33) on which the inner surface of the top of the cap (3) sits.

Figure 3E:
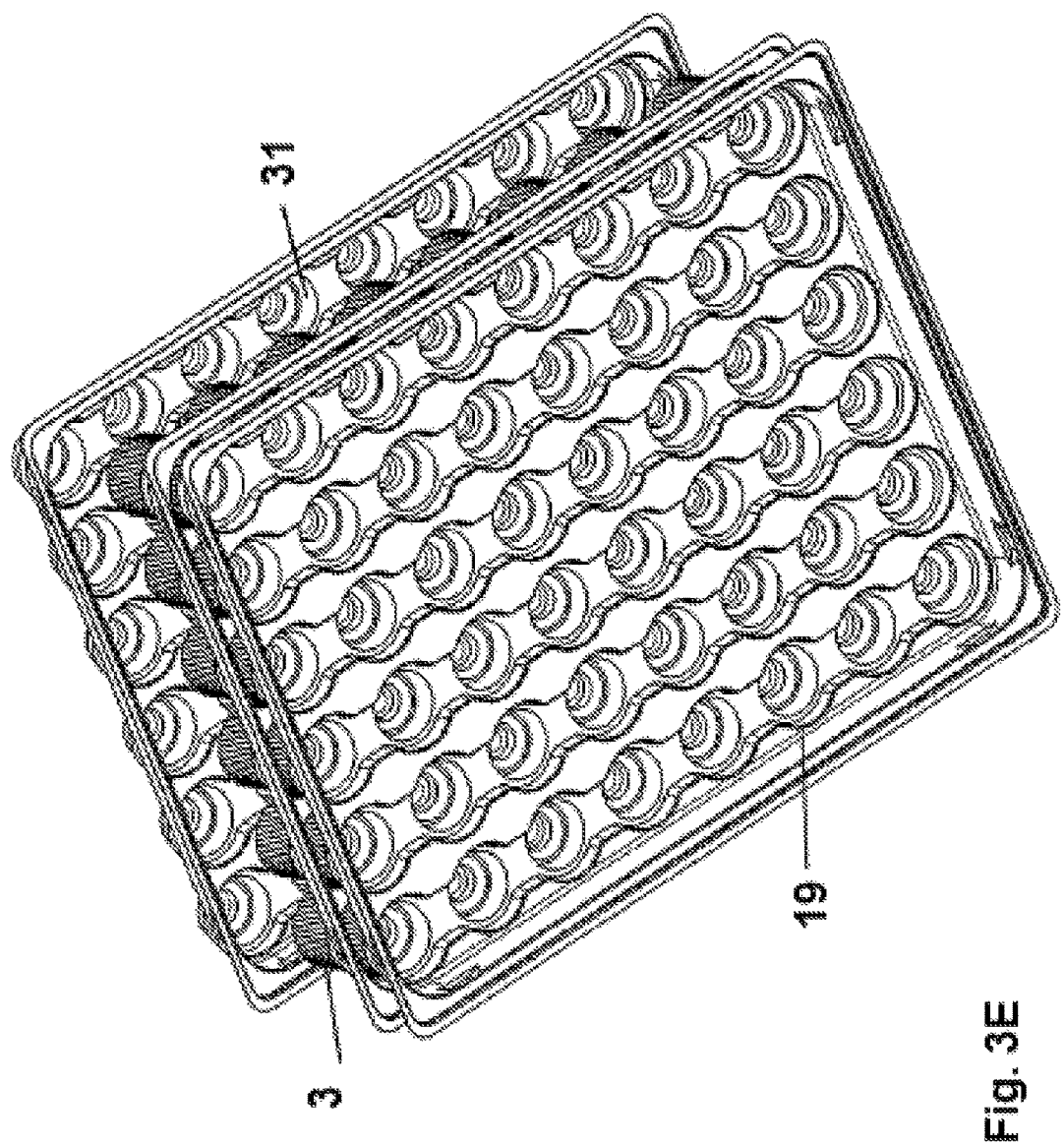
Figure 3F:
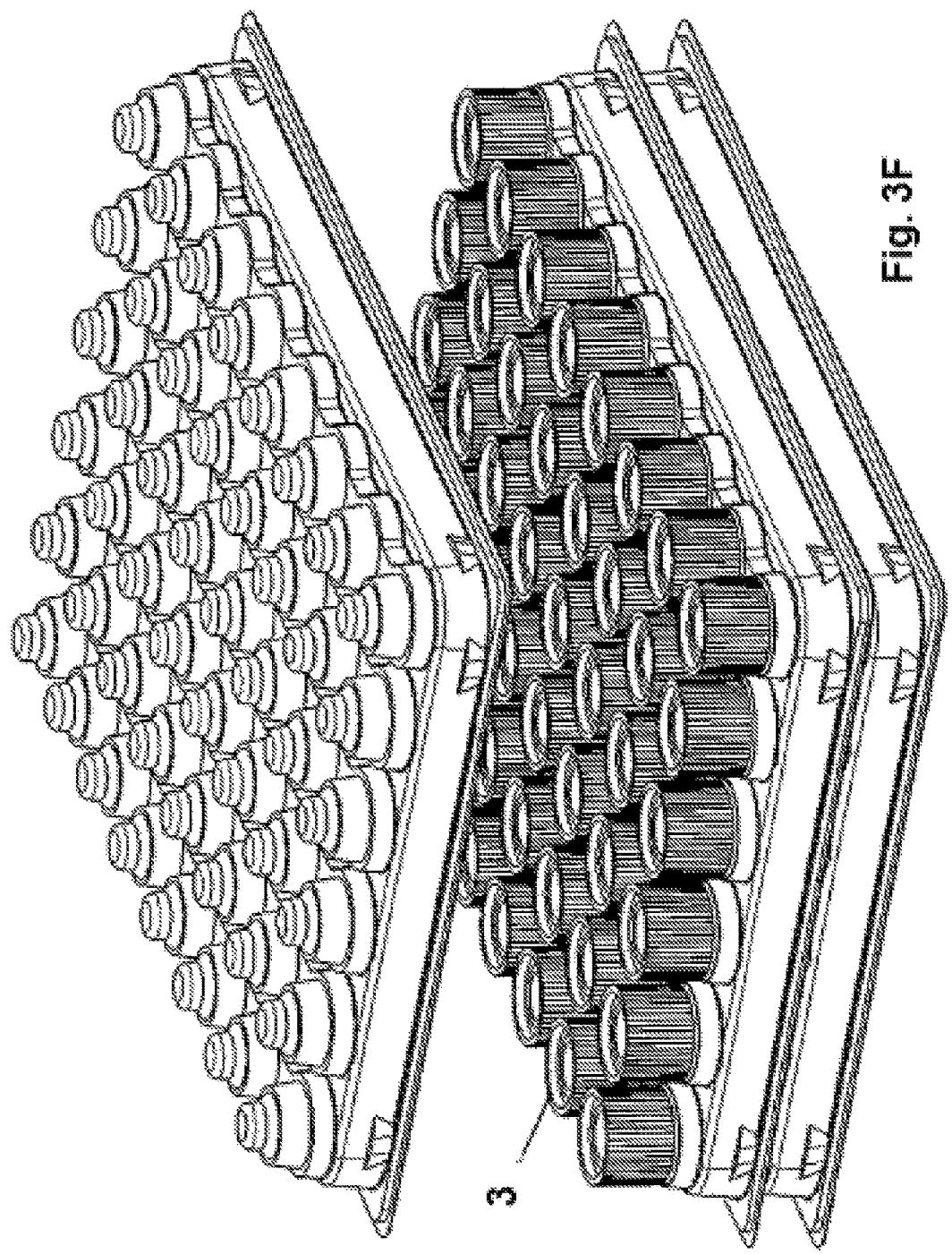

The stack of three cap supplies (2) of FIG. 3C is shown in a perspective view from below in FIG. 3E, with the topmost cap supply (2) slightly lifted, where it becomes evident that the two lower cap supplies (2) are filled with caps (3). The protuberances (19) serving as sockets for the caps (3) have the additional function of providing recesses for the caps (3) of the respective lower cap supply (2) within a stack. In this embodiment, the inner surface of the foot (31) of the protuberance (19) encloses the cap (3) of the lower cap supply (2) in the stack. It can also be seen that the protuberances (19) are interconnected to each other within each row of 8 compartments (12) of the geometrical 8×6 arrangement. The same stack with the slightly lifted topmost cap supply (2) can be seen in a perspective view from above in FIG. 3F.

Figure 4B:
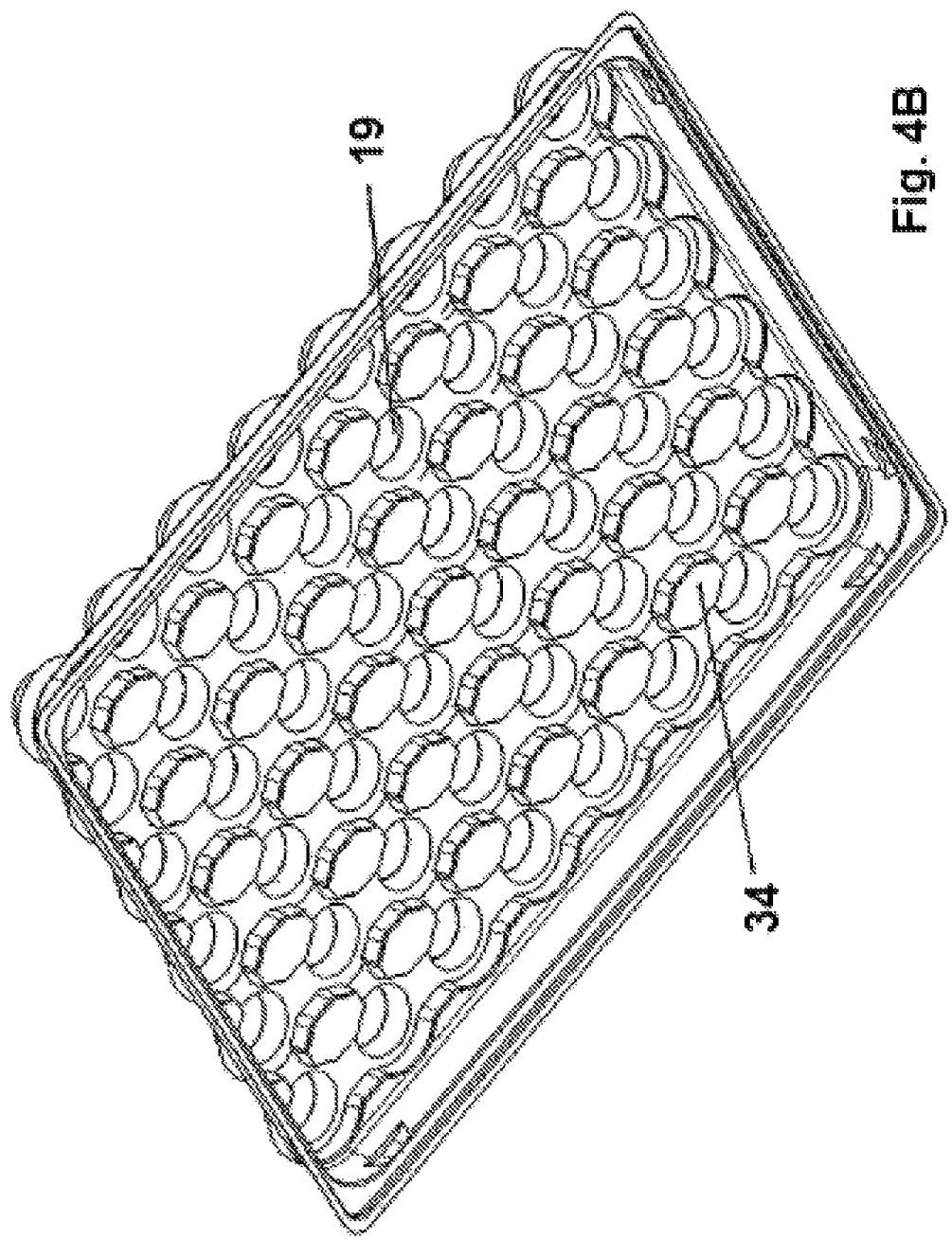

FIG. 4A (perspective view from above) and FIG. 4B (perspective view from below) display a variation of the empty cap supply (2) with compartments (12) in an 8×6 matrix arrangement of FIGS. 3A-F. The protuberances (19) serving as sockets for the caps (3) have essentially the same tripartite structure with foot (31), intermediate ring (32) and top knob (33), while the latter has a smaller diameter than in the embodiment described above, modifying the support stability with regard to the caps (3) placed on the sockets by increasing the clearance between cap (3) and protuberance (19). The figures also exhibit cavities (34) contributing to spatial separation of the compartments (12) and to the overall stability of the cap supply (2).

Figure 5A:
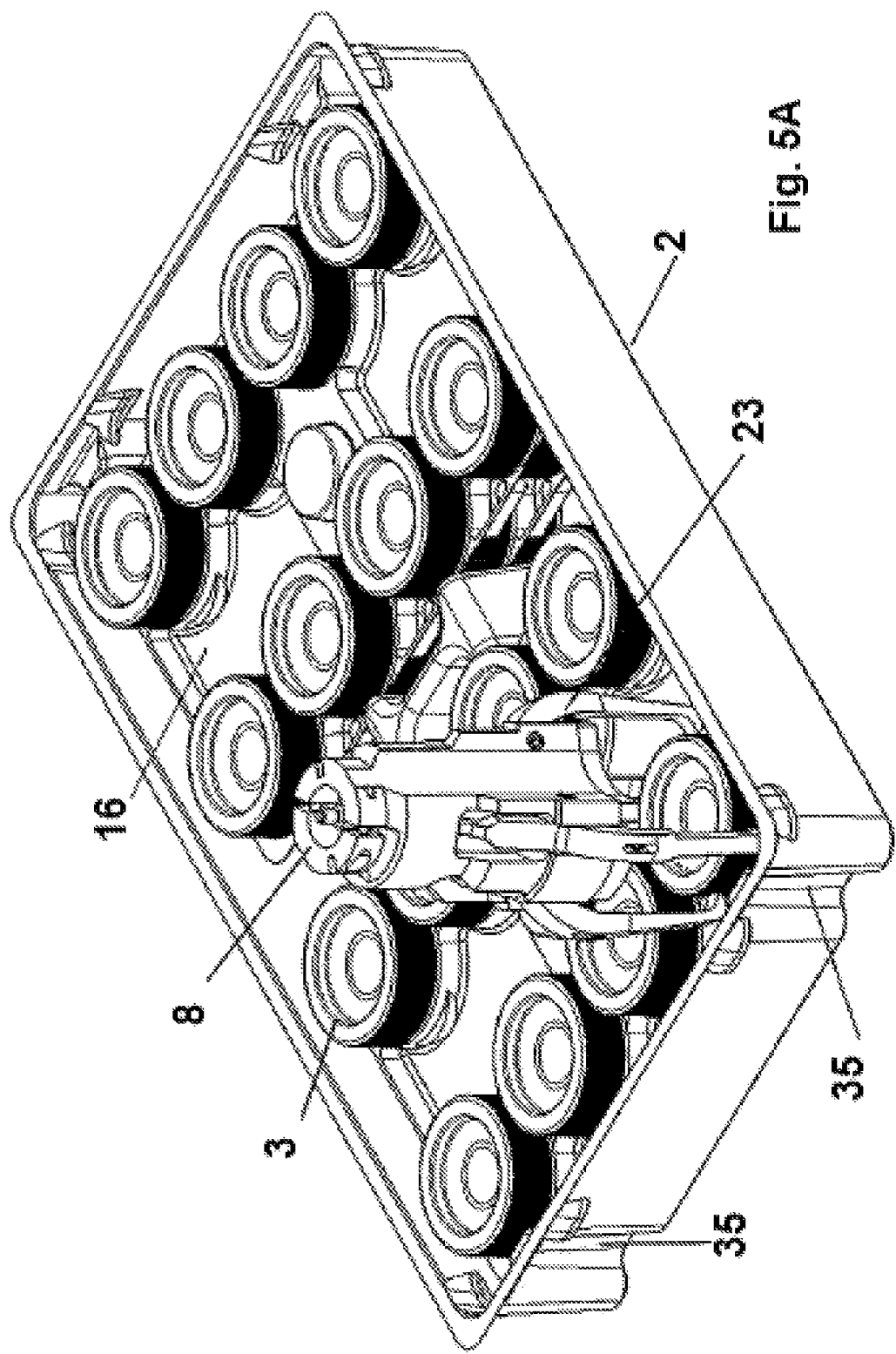

Another embodiment is depicted in FIGS. 5A-G in a perspective view from above, where the cap supply (2) comprises caps (3) accommodated by compartments (12) geometrically arranged in a 4×4 matrix. A cap supply (2) comprising caps (3) can be seen in FIG. 5A, wherein one of the caps (3) is retrieved by a laterally and vertically moveable robotic manipulator (8) which is a robotic gripper in this embodiment. The geometrical arrangement mentioned above provides sufficient space around the caps (3) for the gripper arms (23) to grip the respective cap (3) and retrieve it. As can be also seen in FIG. 5B, the cap supply also comprises recesses (35) at its four corners forming protrusions on its inner walls. These recesses/protrusions (35) contribute to stabilization of the cradles (16) separating the multiple layers (41) of caps (3) and may also serve as a mount for interaction, e.g., with a feeder (7). In this embodiment, three layers (41) of caps (3) are comprised by the cap supply (2). One cradle (16) extends throughout the whole width, but only half the length of the cap supply (2), and thereby separates two layers (41) of 2×4 caps (3) each. The cap supply (2) also comprises a collar (25) along its upper rim which allows the engagement of protrusions (26) comprised by the overhang (27) of a removable lid (20) as depicted in FIG. 5C. The grooves (24) contribute to the stability of the removable lid (20).

Figure 5D:
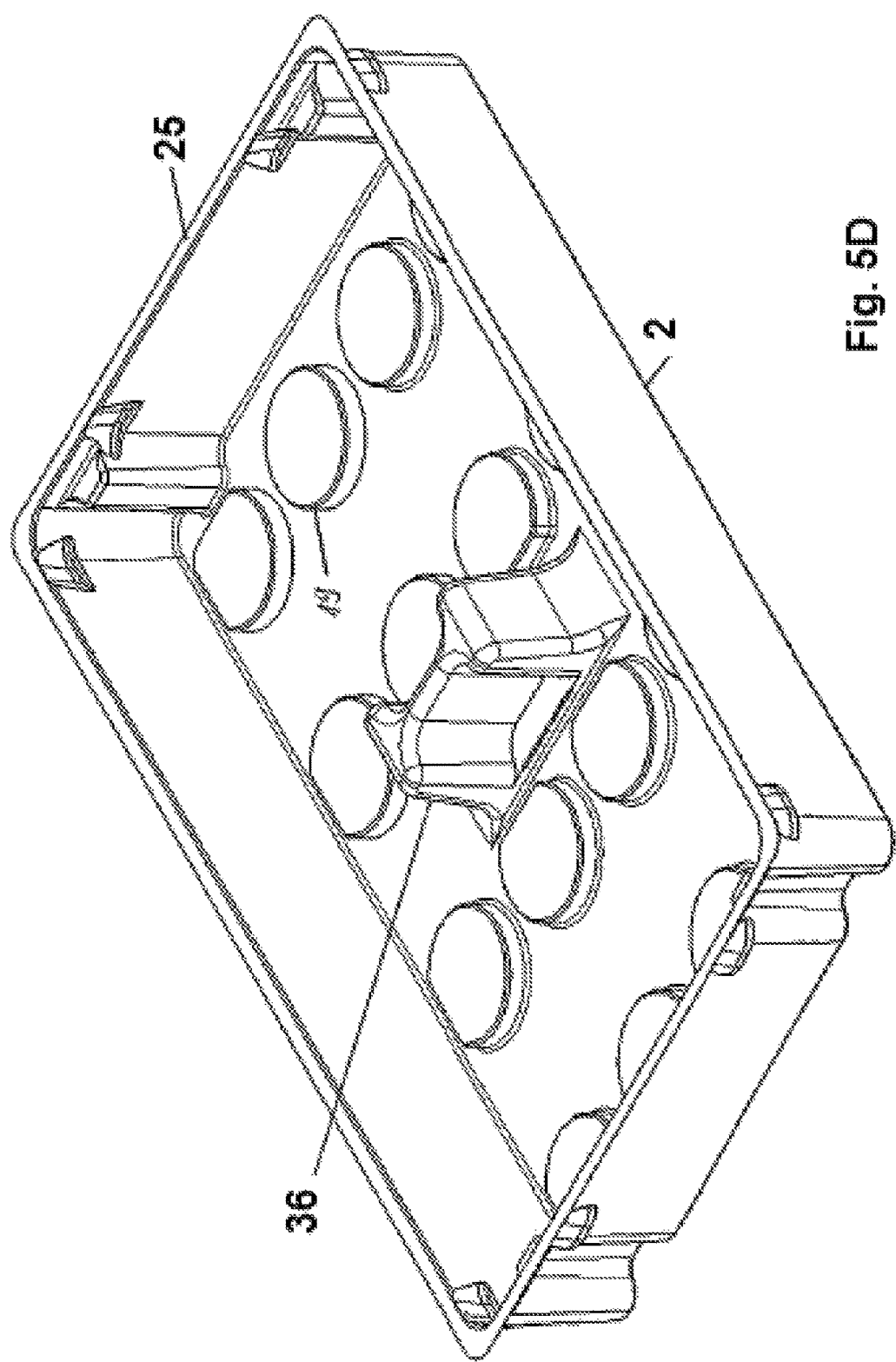

FIG. 5D shows the empty cap supply (2) of this embodiment, wherein the protuberances (19) forming the sockets for the caps (3) at the bottom of the cap supply (2) are visible. Also, a baffle (36) in the center of the cap supply (2) can be seen, wherein the baffle (36) stabilizes the position of the cradles (16).

FIG. 5E (perspective view from above) and FIG. 5F (perspective view from below) show a cradle (16) without caps (3). The 2×4 sockets (37) accommodating the caps (3) can be seen as well as knobs (17) for interaction with a robotic manipulator (8) and protrusions (38) improving the stacking properties of the cradles (16), and also stabilizing the caps (3). The latter are placed on the sockets (37) such that the inner surface of the cap (3) rests on the socket (37). When another cradle (16) is stacked onto a cradle (16) accommodating caps (3), then the socket (37) of the upper cradle (16) receives the cap (3) from the lower cradle (16), thus mechanically stabilizing the stack of cap layers (41). Also, the protrusions (38) improve the stacking properties and the positions of the caps (3).

FIG. 5G shows how a laterally and vertically moveable robotic manipulator (8), in this case a robotic gripper, grips the knob (17) of the empty cradle (16) with its gripping arms (23) to retrieve it from the cap supply (2) and thereby uncover the cap layer (41) underneath.

Figure 6A:
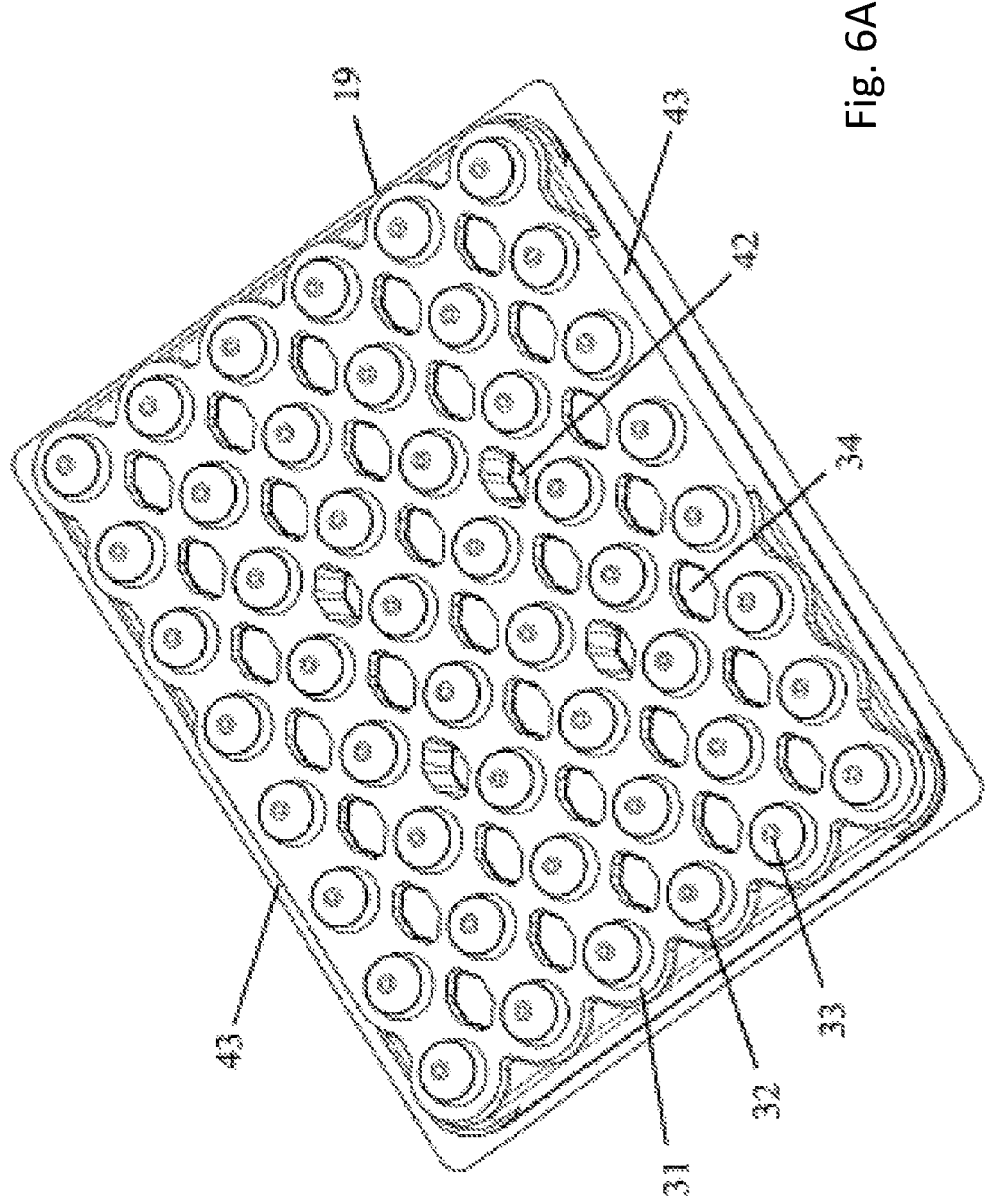
FIGS. 6A-B show perspective views of variation of the cap supply (2) embodiment of FIGS. 4A-B depicted without caps (3).
Figure 6B:
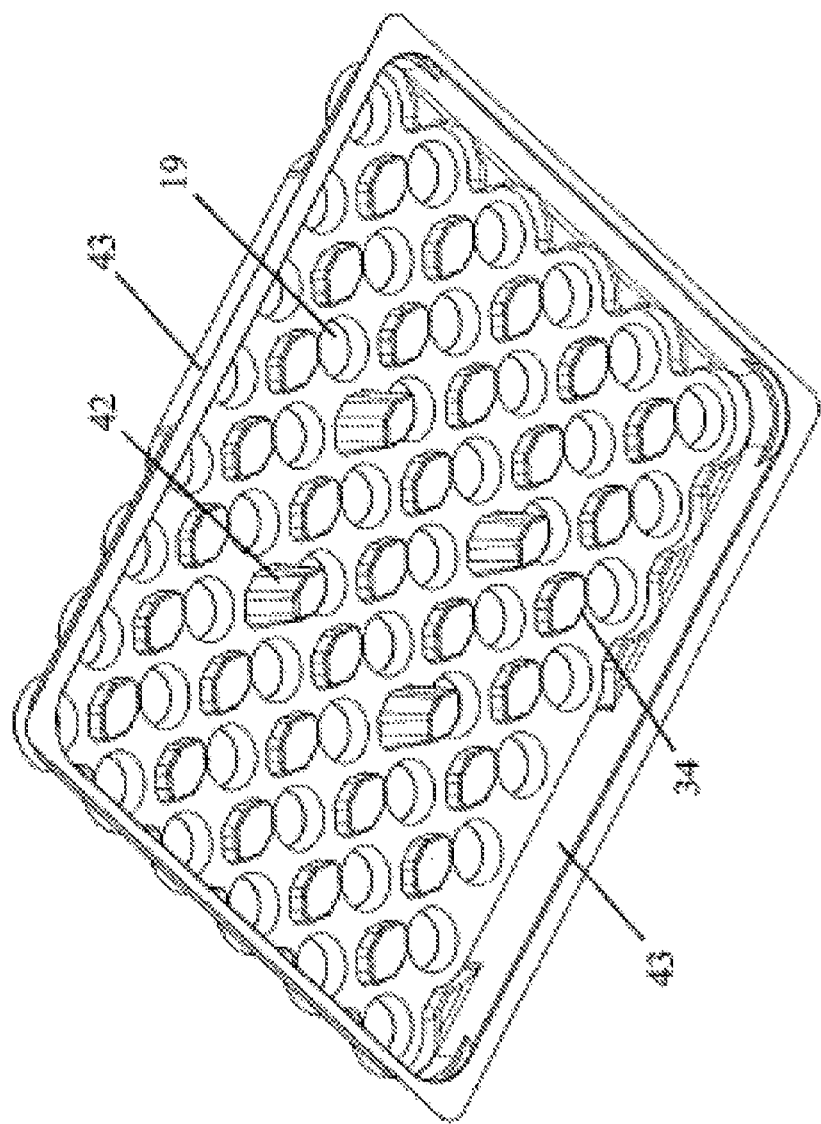

FIG. 6A (perspective view from above) and FIG. 6B (perspective view from below) display a variation of the empty cap supply (2) with compartments (12) in an 8×6 matrix arrangement of FIGS. 4A-B. In addition to the cavities (34) contributing to spatial separation of the compartments (12) and to the overall stability of the cap supply (2), the latter (2) further comprises pillars (42) grouped around its center. These structures increase the cap supply's (2) stability in vertical direction, since the weight of the cap supply (2) itself as well as potentially exerted pressure from above and/or below does not have to be borne exclusively by the outer rim of the cap supply (2). Such pressure may, for example, be exerted when the cap supply (2) is pressed to the feeder (7) from above in order to prevent lateral or vertical movement during interaction with a robotic manipulator (8). The pillars (42) may increase the cap supply's (2) contact area with the feeder (7), especially in embodiments where the feeder (7) has a substantially even surface, such that a cap supply (2) of such an embodiment does not only or not mainly stand on its outer rim. Thus, the pillars (42) also reduce the risk of potential temporary or permanent deformation of the cap supply (2) due to exertion of vertical pressure. This positive effect also facilitates transport and packaging of cap supplies (2) of the current embodiment.

For instance, if multiple cap supplies (2) are stacked on one another in a box, the weight of the upper cap supplies (2) exerts pressure on the lower ones in a stack. Along with the effects of varying ambient conditions during transport or storage such as temperature or moisture, the risk of deformation may, depending on the cap supplies' (2) material, be increased, which can be mitigated by the pillars (42). It can be seen that from above, as in FIG. 6A, the pillars (42) appear as cavities, while they form protuberances when viewed from below as in FIG. 6B. The pillars/protuberances (42) of a cap layer (41) may be engaged to the pillars/cavities (42) of another cap layer (42) directly underneath which may facilitate stacking of multiple cap layers (41). While this depiction shows four pillars (42), more or fewer pillars (42) may be present. Also, other geometrical arrangements are possible with a similar contribution to the beneficial effects described above. The plain stretches (43) along the otherwise rippled outer line of the cap supply (2) may serve as an application area for an identification tag (14) like, for instance, a barcode (see FIG. 2D).

While the foregoing embodiments have been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A cap supply comprising a plurality of caps for one or more vessels containing biological samples, wherein the cap supply comprises
    a mount including a plurality of compartments that accommodate the plurality of caps, wherein the plurality of compartments are positioned within the mount in a predefined geometrical arrangement,
    wherein one or more compartments of the plurality of compartments comprise two or more caps stacked to form one or more layers, each compartment including a socket sized to fit an inner surface of a cap,
    each of the one or more layers are separated in the compartment by one or more cradles each comprising two or more protrusions positioned on the one or more cradles between the plurality of compartments, wherein the two or more protrusions facilitate stacking of the one or more cradles and stabilize the plurality of caps, and
    the cap supply further comprises a baffle positioned in a center of the cap supply to stabilize the one or more cradles in the cap supply.

2. The cap supply of claim 1, wherein each of the compartments comprise free space around each cap sufficient for a laterally and vertically moveable robotic gripper to retrieve one of the plurality of caps from one of the plurality of compartments.

3. The cap supply of claim 1, wherein a bottom surface of each compartment comprises a protuberance for supporting a cap.

4. The cap supply of claim 1, wherein the cap supply is stackable.

* * * * *